United States Patent [19]
Mjalli et al.

[11] Patent Number: 5,700,826
[45] Date of Patent: Dec. 23, 1997

[54] 1,2,4,5-TETRA SUBSTITUTED IMIDAZOLES AS MODULATORS OF MULTI-DRUG RESISTANCE

[75] Inventors: Adnan Mjalli, Vista; Sepehr Sarshar, Cardiff by the Sea, both of Calif.

[73] Assignee: Ontogen Corporation, Carlsbad, Calif.

[21] Appl. No.: 481,118

[22] Filed: Jun. 7, 1995

[51] Int. Cl.$^6$ .............. A01K 31/415; C07D 233/04; C07D 233/61; C07D 233/56

[52] U.S. Cl. .............. 514/397; 514/398; 514/399; 546/94; 548/315.4; 548/338.1; 548/335.5; 548/343.5

[58] Field of Search .............. 548/335.5, 338.1, 548/343.5, 315.4; 546/94; 514/397, 398, 399

[56] References Cited

U.S. PATENT DOCUMENTS

| | | | |
|---|---|---|---|
| 2,801,243 | 7/1957 | Hanslick et al. | 548/315.4 X |
| 3,361,755 | 1/1968 | Green | 548/343.5 X |
| 3,558,645 | 1/1971 | Griot | 548/343.5 |
| 3,707,475 | 12/1972 | Lombardino | 548/343.5 X |
| 4,424,229 | 1/1984 | Jorgensen et al. | 548/343.5 X |
| 4,632,930 | 12/1986 | Carini et al. | 514/365 |
| 4,665,023 | 5/1987 | Deneke et al. | 435/28 |
| 4,914,096 | 4/1990 | Houlihan et al. | 514/220 |
| 5,274,095 | 12/1993 | Braun et al. | 546/94 |
| 5,292,669 | 3/1994 | Guder et al. | 435/18 |
| 5,296,609 | 3/1994 | McCort et al. | 548/325.1 |
| 5,312,828 | 5/1994 | Finkelstein et al. | 514/381 |

FOREIGN PATENT DOCUMENTS

| | | | |
|---|---|---|---|
| 0044486 | 1/1982 | European Pat. Off. | 548/335.5 |
| 0582164 | 2/1994 | European Pat. Off. | |
| 3835195 | 4/1990 | Germany | 548/343.5 |
| 42-006750 | 3/1967 | Japan | 548/335.5 |
| 61-174267 | 8/1986 | Japan | 548/343.5 |
| 63-208570 | 8/1988 | Japan | 548/343.5 |
| 3-232861 | 10/1991 | Japan | 548/343.5 |
| 4-279569 | 10/1992 | Japan | 548/343.5 |
| 0454154 | 6/1968 | Switzerland | 548/343.5 |
| WO9314081 | 7/1993 | WIPO . | |
| WO9314082 | 7/1993 | WIPO . | |

OTHER PUBLICATIONS

N. Engel et al., "Imidazole und 1–Imidazolamine aus a–Acylaminoketiminen und a–Acylaminohydrazonen", Liebigs Ann. Chem., 1978, 1916–1927.

I. Matsuda et al., "Cyclization Reactions by the Use of 1,2-Bis(Trimethylsilyl) Imino–1,2–Diphenylethane", Chemistry Letters, pp. 1456–1460, 1977.

A. Novelli et al., "General Synthesis of C Substituted Imidazoles", Tetrahedron Letters No. 3, pp. 265–269, 1967.

A. Palkowitz et al., "Structural Evolution and Pharmacology of a Novel Series of Triacid Angiotensin II Receptor Antagonists", J. Med. Chem., 1994, 37, 4508–4521.

A. Salimbeni et al., "Nonpeptide Angiotensin II Receptor Antagonists. Synthesis, in Vitro Activity, and molecular modeling Studies of N–[Heterobiaryl]methyllimidazoles", J. Med. Chem., 1994, 37, 3928–3938.

Primary Examiner—Floyd D. Higel
Attorney, Agent, or Firm—Frank S. Chow

[57] ABSTRACT

This invention relates to compounds of Formula 1 which are pharmacologically useful for the treatment of cancer through sensitization of multi-drug resistant cancer cells to chemotherapeutic agents.

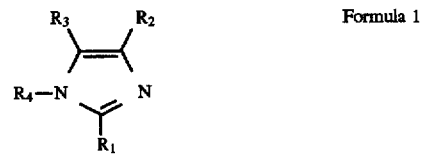

Formula 1 wherein $R_1$, $R_2$, $R_3$, and $R_4$ are, respectively hydrogen, alkyl, alkenyl, substituted alkyl, substituted alkenyl, aryl, substituted aryl.

39 Claims, No Drawings

1,2,4,5-TETRA SUBSTITUTED IMIDAZOLES AS MODULATORS OF MULTI-DRUG RESISTANCE

FIELD OF THE INVENTION

The present invention provides novel imidazole derivatives, novel pharmaceutical compositions containing same, methods of their use, and methods of their manufacture. Such compounds are pharmacologically useful for restoring the sensitivity of multidrug resistant cells to cancer chemotherapeutic agents.

BACKGROUND OF THE INVENTION

A major problem in the treatment of malignancies of the blood and solid tumors is the emergence of tumor cell resistance to chemotherapeutic agents and the subsequent patient relapse (Bradley et al., *Cancer Res.* 49: 2790–2796, 1989; Raderer and Scheithaurer, *Cancer* 72: 3553–3563, 1993). This resistance causes cancer victims to fail to respond to any antitumor agent, since the transformed tumor cells tend to exhibit clinical resistance to many drugs. The emergence of the resistant cells to multiple chemotherapeutic agents occurs either at the initial presentation (intrinsic resistance) or at the time of relapse (acquired resistance). Both of these phenomena are known as multi-drug resistance (MDR). MDR is associated with certain alterations in tumor cells resulting in reduced intracellular anticancer drug accumulation, including reduced membrane permeability and increased removal of drug from the cell via an energy-dependent efflux mechanism. Studies of this mechanism have led to the characterization of genes capable of conferring resistance to chemotherapeutic agents. One of these genes, the P-glycoprotein or MDR1 gene, has been strongly implicated since overexpression of this gene can lead to resistance to anthracyclines, vinca alkaloids, and podophyllins, all important chemotherapeutic agents. MDR1 encodes a 170 kDa membrane glycoprotein (gp-170 or Pgp) that acts as an ATP-dependent efflux pump, transporting a number of unrelated organic compounds out of the cell (Juranka et al., *FASEB J.* 3:2583–2592, 1989). The level of expression of gp-170 has been shown to correlate with the degree of drug resistance (Raderer and Scheithaurer, *Cancer* 72: 3553–3563, 1993). gp-170 appears to act as a pump that actively extrudes a wide variety of structurally unrelated compounds, including a full range of antineoplastic drugs. Another ATP-dependent membrane efflux pump, the product of the MRP gene, has also been implicated in the MDR phenomenon (Krishnamachary and Center, *Cancer Res.* 53: 3658–3661, 1993), as have other ATP-dependent and enzymatic mechanisms.

Drugs of proven antitumor chemotherapeutic value to which MDR has been observed include vinblastine, vincristine, etoposide, teniposide, doxorubicin (adriamycin), daunorubicin, pliamycin (mithramycin), and actinomycin D (Jones et al., *Cancer* (Suppl) 72: 3484–3488, 1993). Many tumors are intrinsically multi-drug resistant (e.g., adenocarcinomas of the colon and kidney) while other tumors acquire MDR during the course of therapy (e.g., neuroblastomas and childhood leukemias).

A variety of structurally diverse agents have been identified which can restore partially or sometimes completely the normal drug sensitivity to some MDR tumor cells. It is assumed that these chemosensitizers are effective as a result of their ability to interfere with gp-170, causing a reversal in the increase in drug efflux. Among these agents are calcium channel blockers (e.g., verapamil and nifedipine), calmodulin inhibitors (e.g., trifluoperazine), antibiotics (e.g., erythromycin), cardiovascular agents (e.g., quinidine), non-cytotoxic analogs of anthracyclines and vinca alkaloids, the clinically useful immunosuppressants cyclosporin A (and analogs thereof) and FK-506 (and analogs thereof), and derivatives of cyclopeptides (Lure et al., *Cancer* (Suppl) 72: 3502–3514, 1993). However, at the present time, none of these agents has provided a significant contribution to the chemotherapeutic index for the treatment of cancer due to their significant pharmacological effects on other organ systems. An effective therapeutic agent for the reversal of MDR needs to have efficacy against the membrane pump as well as lack significant toxicity and other non-specific pharmacological effects.

The present invention describes a family of novel substituted imidazole derivatives that are effective in increasing the sensitivity of tumor cells resistant to anticancer chemotherapeutic agents, such as doxorubicin (DOX), taxol, and vinblastine (VLB), and enhancing the sensitivity of multi-drug resistant cells. These compounds have the effect of reducing the resistance of MDR tumor cells, and potentiating the sensitivity of cells to antitumor drugs, such as DOX, taxol, and VLB. These compounds are expected to have broad application in the chemotherapy of cancer.

It is an object of this invention, therefore, to provide compounds that have sufficient activity to sensitize multi-drug resistant tumor cells to antineoplastic agents.

It is an additional object of this invention to provide a method of sensitizing multi-drug resistant tumor cells using the novel compounds of the present invention.

A further object is to provide a method of treatment of MDR or drug-sensitive tumor cells by administering a sufficient amount of a compound of the present invention, prior to, together with, or subsequent to the administration of an antitumor chemotherapeutic agent.

A further object is to provide pharmaceutical compositions for increasing the sensitivity of tumor cells to antitumor chemotherapeutic agents and thus for the treatment of tumors that are susceptible to anti-cancer chemotherapeutic agents but have become resistant to such chemotherapy.

These and other objects will be apparent from the following description.

SUMMARY OF THE INVENTION

The novel compounds of this invention have the general formula

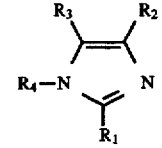

and are capable of restoring sensitivity to multi-drug resistant tumor cells.

It is an object of this invention to provide compounds that have sufficient activity to sensitize multi-drug resistant tumor cells to antineoplastic agents.

It is an additional object of this invention to provide a method of sensitizing multi-drug resistant tumor cells using the novel compounds of the present invention.

A further object is to provide a method of treatment of MDR or drug-sensitive tumor cells by administering a sufficient amount of a compound of the present invention, prior to, together with, or subsequent to the administration of an antitumor chemotherapeutic agent.

A further object is to provide pharmaceutical compositions for increasing the sensitivity of tumor cells to antitumor chemotherapeutic agents and thus for the treatment of tumors that are susceptible to anti-cancer chemotherapeutic agents but have become resistant to such chemotherapy.

DETAILED DESCRIPTION OF THE INVENTION

The present invention encompasses compounds of general structural Formula 1

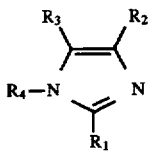

Formula 1 or a pharmaceutically acceptable salt, ester, or prodrug thereof wherein:

$R_1$ is:
(a) substituted $C_{1-11}$ alkyl or substituted $C_{2-11}$ alkenyl, wherein the substituent is selected from the group consisting of hydrogen, hydroxy, halo, $C_{1-6}$ alkyloxy, $C_{1-6}$ alkylthio, $C_{1-6}$ alkylamino, phenyl-$C_{1-6}$ alkyloxy, phenyl-$C_{1-6}$ alkylthio, and phenyl-$C_{1-6}$ alkylamino; or
(b) aryl-$C_{0-11}$-alkyl, wherein the aryl group is selected from the group consisting of phenyl, naphthyl, pyridyl, furyl, pyrryl, thienyl, isothiazolyl, imidazolyl, benzimidazolyl, tetrazolyl, pyrazinyl, pyrimidyl, quinolyl, isoquinolyl, benzofuryl, benzothienyl, pyrazolyl, indolyl, isoindolyl, purinyl, carbazolyl, isoxazolyl, thiazolyl, oxazolyl, benzthiazolyl, and benzoxazolyl; and mono-, di-, and tri-substituted-aryl $C_{0-11}$-alkyl wherein aryl is as defined above and wherein the substituents are independently selected from
(a) trifluoromethyl,
(b) hydroxy,
(c) halo,
(d) phenyl, trans-2-phenylethenyl, 2-phenylethynyl, 2-phenylethyl, wherein the phenyl group is optionally mono- or di-substituted with hydroxy, halo, $C_{1-4}$ alkyl, or $C_{1-4}$ alkyloxy,
(e) carboxy,
(f) amino,
(g) optionally substituted $C_{1-6}$ alkyl, $C_{1-6}$ alkyloxy, $C_{1-6}$ alkylthio, $C_{1-6}$ alkylamino, $C_{1-6}$ alkylcarbonyl, $C_{1-6}$ alkylcarbonylamino, $C_{1-6}$ alkylaminocarbonyl, $C_{1-6}$ alkoxycarbonyl, wherein the substituent is selected from the group consisting of amino, carboxy, $C_{1-6}$ alkoxy, $C_{1-6}$ alkylthio, $C_{1-6}$ alkylamino, and di-($C_{1-6}$) alkylamino,
(h) $C_{1-11}CO_2R_5$, $C_{1-11}CONHR_5$, trans-CH=CHCO$_2$R$_5$, or trans-CH=CHCONHR$_5$ wherein $R_5$ is hydrogen, $C_{1-11}$ alkyl, or phenyl$C_{1-11}$ alkyl,
(i) carboxymethyleneoxy, and
(j) $C_{1-6}$ alkoxycarbonylmethyleneoxy;

$R_2$ and $R_3$ are each independently:
aryl wherein the aryl group is as defined under the definition of $R_1$ above; and mono-, di-, and tri-substituted aryl wherein the substituents are independently selected from hydroxy, halo, trifluoromethyl, $C_{1-6}$ alkyl, $C_{1-6}$ alkyloxy, $C_{1-6}$ alkylthio, amino, $C_{1-6}$ alkylamino, di-($C_{1-6}$ alkyl)-amino, phenyl-$C_{1-6}$ alkylamino, and di-(phenyl-$C_{1-6}$ alkyl) amino; and $R_4$ is:
(a) hydrogen;
(b) substituted $C_{1-11}$ alkyl or $C_{2-11}$ alkenyl wherein the substituent is selected from the group consisting of hydrogen, hydroxy, halo, $C_{1-6}$ alkyloxy, $C_{1-6}$ alkylthio, $C_{1-6}$ alkylamino, phenyl-$C_{1-6}$ alkyloxy, phenyl-$C_{1-6}$ alkylthio, and phenyl-$C_{1-6}$ alkylamino, carboxy, and $C_{1-6}$ alkoxycarbonyl; or
(c) aryl $C_{0-11}$ alkyl wherein the aryl group is as defined under the definition of $R_1$ above; and mono-, di-, and tri-substituted-aryl $C_{0-11}$-alkyl wherein aryl is as defined above and wherein the substituents are independently selected from $C_{1-6}$ alkyl, trifluoromethyl, hydroxy, halo, $C_{1-6}$ alkyloxy, amino, $C_{1-6}$ alkylamino, amino$C_{1-6}$ alkyl, carboxy, and carboxy$C_{1-6}$ alkyl.

A preferred embodiment concerns compounds wherein:
$R_1$ is aryl, wherein the aryl group is selected from the group consisting of phenyl, naphthyl, pyridyl, furyl, pyrryl, thienyl, imidazolyl, benzimidazolyl, pyrimidyl, quinolyl, isoquinolyl, benzofuryl, benzothienyl, indolyl, thiazolyl, oxazolyl, benzthiazolyl, and benzoxazolyl; and mono- and di-substituted-aryl wherein aryl is as defined above and wherein the substituents are independently selected from
(a) hydroxy,
(b) halo,
(c) phenyl, trans-2-phenylethenyl, wherein the phenyl group is optionally mono- or di-substituted with hydroxy, halo, $C_{1-4}$ alkyl, or $C_{1-4}$ alkyloxy,
(d) carboxy,
(e) amino,
(f) optionally substituted $C_{1-6}$ alkyl, $C_{1-6}$ alkyloxy, $C_{1-6}$ alkylthio, $C_{1-6}$ alkylamino, $C_{1-6}$ alkoxycarbonyl, wherein the substituent is selected from the group consisting of amino, carboxy, $C_{1-3}$ alkoxy, $C_{1-3}$ alkylthio, $C_{1-3}$ alkylamino, and di-($C_{1-3}$) alkylamino,
(g) trans-CH=CHCO$_2$R$_5$, or trans-CH=CHCONHR$_5$ wherein $R_5$ is hydrogen or $C_{1-6}$ alkyl,
(h) carboxymethyleneoxy, and
(i) $C_{1-6}$ alkoxycarbonylmethyleneoxy;

$R_2$ and $R_3$ are each independently phenyl and mono- and di-substituted phenyl wherein the substituents are independently selected from hydroxy, halo, trifluoromethyl, $C_{1-6}$ alkyl, $C_{1-6}$ alkyloxy, $C_{1-6}$ alkylthio, amino, $C_{1-6}$ alkylamino, and di-($C_{1-6}$ alkyl)-amino; and $R_4$ is hydrogen; substituted $C_{1-6}$ alkyl, wherein the substituent is selected from the group consisting of hydrogen, hydroxy, halo, $C_{1-6}$ alkyloxy, $C_{1-6}$ alkylthio, $C_{1-6}$ alkylamino, carboxy, and $C_{1-6}$ alkoxycarbonyl; or mono- or di-substituted aryl $C_{0-3}$ alkyl, wherein the aryl group is selected from the group consisting of phenyl, pyridyl, furyl, thienyl, imidazolyl, thiazolyl, and oxazolyl, and wherein the substituents are independently selected from hydrogen, $C_{1-6}$ alkyl, trifluoromethyl, hydroxy, halo, $C_{1-6}$ alkyloxy, amino, $C_{1-6}$ alkylamino, amino$C_{1-6}$ alkyl, carboxy, and carboxy$C_{1-6}$ alkyl.

A still more preferred group comprises compounds wherein:

$R_1$ is mono- or di-substituted phenyl, wherein the substituents are selected from the group consisting of
(a) hydroxy,
(b) trans-2-phenylethenyl, wherein the phenyl group is optionally mono- or di-substituted with hydroxy, halo, $C_{1-4}$ alkyl, or $C_{1-4}$ alkyloxy,
(c) carboxy,
(d) optionally substituted $C_{1-4}$ alkyl, $C_{1-4}$ alkyloxy, $C_{1-4}$ alkylthio, $C_{1-4}$ alkylamino, $C_{1-4}$ alkoxycarbonyl, wherein the substituent is selected from the group consisting of amino, carboxy, $C_{1-3}$ alkoxy, $C_{1-3}$ alkylthio, $C_{1-3}$ alkylamino, and di-($C_{1-3}$) alkylamino,
(e) trans-CH=CHCO$_2$R$_5$, or trans-CH=CHCONHR$_5$ wherein $R_5$ is hydrogen or $C_{1-4}$alkyl, (f) carboxymethyleneoxy, and (g) $C_{1-4}$alkoxycarbonylmethyleneoxy;

$R_2$ and $R_3$ are each independently phenyl or monosubstituted phenyl wherein the substituent is selected from the group consisting of $C_{1-3}$ alkyl, $C_{1-3}$ alkyloxy, amino, $C_{1-3}$ alkylamino, and di-$(C_{1-3}$ alkyl)amino; and $R_4$ is hydrogen; substituted $C_{1-6}$ alkyl, wherein the substituent is selected from the group consisting of hydrogen, carboxy, and $C_{1-3}$ alkoxycarbonyl; or mono-substituted aryl $C_{0-3}$ alkyl, wherein the aryl group is selected from the group consisting of phenyl, pyridyl, and imidazolyl and wherein the substituent is selected from the group consisting of hydrogen, $C_{1-4}$ alkyl, trifluoromethyl, hydroxy, halo, $C_{1-4}$ alkyloxy, amino, $C_{1-4}$ alkylamino, carboxy, and carboxy$C_{1-4}$ alkyl.

Novel compounds of the present invention include but are not limited to the following compounds:

2-(4-hydroxyphenyl)-1,4,5 -triphenyl-imidazole trifluoroacetic acid salt;

1-benzyl-2-(4-hydroxyphenyl)-4,5-di-(4-methoxyphenyl)-imidazole trifluoroacetic acid salt;

2-(4-carboxyphenyl)-4,5-di-[4-(dimethylamino)-phenyl]-1(H)-imidazole;

4,5-di-[4-(dimethylamino)-phenyl]-2-[4-(methoxycarbonyl)-phenyl]-1(H)-5 imidazole;

2-(4-carboxyphenyl)-4,5 -di-[4-(dimethylamino)-phenyl]-1-(n-hexyl)-imidazole;

4,5-di-[4-(dimethylamino)-phenyl]-1-(n-hexyl)-2-[4-(methoxycarbonyl)-phenyl]-imidazole;

2-[4-(trans-2-carboxyethenyl) -phenyl]-4,5-di-[4-(dimethylamino)-phenyl]-1(H)-imidazole;

4,5-di-[4-(dimethylamino)-phenyl]-2-{4-[trans-(2-methoxycarbonyl)-ethenyl]-phenyl}-1(H)-imidazole;

4,5 -di-[4-(dimethylamino)-phenyl]-2-(4-hydroxyphenyl)-1(H)-imidazole;

4,5-di-[4-(dimethylamino)-phenyl]-2-(4-hydroxyphenyl)-1-(2-phenylethyl)-imidazole;

2-(4-carboxyphenyl)-4,5-di-[4-(dimethylamino)-phenyl]-1-(2-phenylethyl)-imidazole;

2-[4-(trans-2-carboxyethenyl)-phenyl]-4,5-di-[4-(dimethylamino)-phenyl]-1-(2-phenylethyl)-imidazole;

4,5-di-(4-methoxyphenyl)-2-{4-[trans-(2-methoxycarbonyl)-ethenyl]-phenyl }-1-[5-(methoxycarbonyl)-n-pentyl)-imidazole;

2-(trans-4-stilbenyl)-1-[3-(imidazol-1-yl)-n-propyl]-4,5-di-(4-methoxyphenyl)-imidazole;

4,5-di-[4-(dimethylamino)-phenyl]-2-{4-[trans-(2-methoxycarbonyl)-ethenyl]-phenyl}-1-[5-(methoxycarbonyl)-n-pentyl-]-imidazole;

4,5-di-(4-methoxyphenyl)-2-{4-[3-(dimethylamino)-propyloxy]-phenyl }-1-(n-hexyl)-imidazole;

4,5-di-(4-methoxyphenyl)-2-{4-[3-(dimethylamino)-propyloxy]-phenyl}-1-[3-(imidazol-1-yl)-n-propyl]-imidazole.

As used herein "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonyl, decyl, iso-propyl (i-Pr), iso-butyl (i-Bu), tert-butyl (t-Bu), sec-butyl (s-Bu), iso-pentyl, and the like, as well as saturated alicyclic hydrocarbon groups having the specified number of carbon atoms, e.g., cyclopentyl, cyclohexyl, and the like. "Alkyloxy" (or "alkoxy") represents an alkyl group having the indicated number of carbon atoms attached through the oxygen bridge, e.g., methoxy, ethoxy, propyloxy, and the like. "Alkenyl" is intended to include hydrocarbon groups of either a straight or branched configuration with one or more carbon—carbon double bonds which may occur in any stable point along the chain, such as ethenyl, propenyl or allyl, butenyl, pentenyl, 1,5-octadienyl, and the like. The carbon—carbon double bonds may have either the cis- or trans -configuration.

The term "halo" means fluoro, chloro, bromo, or iodo.

The term "prodrug" refers to a compound that is made more active in vivo.

Pharmaceutically acceptable salts of the compounds of formula 1, where a basic or acidic group is present in the structure, are also included within the scope of this invention. When an acidic substituent is present, such as —COOH and $P(O)(OH)_2$, there can be formed the ammonium, calcium, magnesium, sodium, potassium salt, and the like, for use as the dosage form. Salts derived from pharmaceutically acceptable organic non-toxic bases include salts of primary, secondary, and tertiary amines, substituted amines including naturally occurring substituted amines, cyclic amines, and basic ion-exchange resins, such as arginine, betaine, caffeine, choline, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When a basic group is present, such as amino or a basic heteroaryl radical, such as pyridyl, an acidic salt, such as hydrochloride, hydrobromide, acetate, maleate, pamoate, methanesulfonate, p-toluenesulfonate, and the like, can be used as the dosage form.

Also, in the case of the —COOH or —$P(O)(OH)_2$ being present, pharmaceutically acceptable esters can be employed, e.g., methyl, tert-butyl, pivaloyloxymethyl, and the like, and those esters known in the art for modifying solubility or hydrolysis characteristics for use as sustained release or prodrug formulations.

In addition, some of the compounds of the instant invention may form solvates with water or common organic solvents. Such solvates are encompassed within the scope of the invention.

The term "therapeutically effective amount" shall mean that amount of drug or pharmaceutical agent that will elicit the biological or medical response of a tissue, system, animal, or human that is being sought by a researcher, veterinarian, medical doctor or other clinician.

The compounds of the present invention are conveniently prepared using either solid-phase or solution phase synthetic methods. These two methods are described generally below and depicted in the following reaction Schemes. Where appropriate, the synthetic methods utilize readily available starting materials, reagents, and conventional synthetic procedures. In these reactions, it is also possible to make use of variants which are themselves known to those of ordinary skill in this art, but are not mentioned in greater detail.

The solid-phase methods, which are depicted in Schemes 1 and 4, employ either an aldehyde linker or a FMOC-amino acid linker on solid supports.

The solid-phase method using an aldehyde linker (Scheme 1) involves synthesis of the substituted imidazoles of the present invention by reaction of an aryl aldehyde linked to a solid support of general formula 3 with a 1,2-diarylethanedione of general formula 1 in the presence of an amine ($R_4NH_2$) of general formula 2 and ammonium acetate and subsequent cleavage of the desired substituted imidazole from the solid support with trifluoroacetic acid to afford compounds of general formula 4. The solid supports of general formula 3 comprise either a carboxyaldehyde resin or an alkoxyaldehyde resin.

SCHEME 1

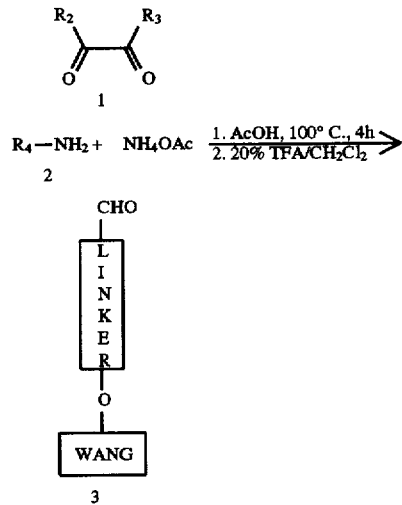

SCHEME 2

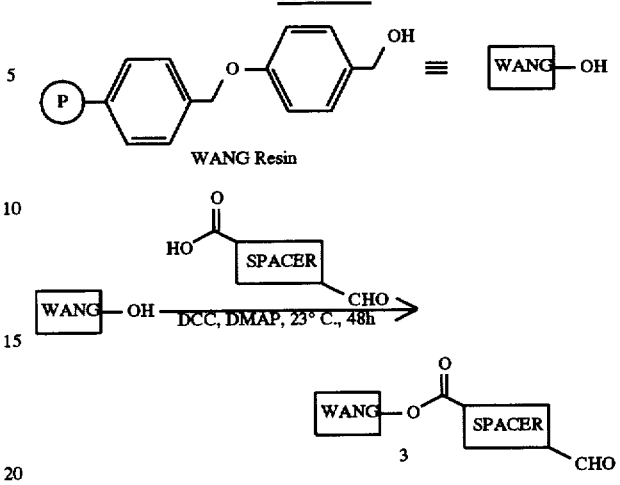

The synthesis of the carboxyaldehyde resin of general formula 3 is shown in Scheme 2 and employs methodologies described by Lu et al., *J. Org. Chem.* 46: 3433, 1981. A typical procedure involves reacting 6 mmol (1 equiv) of Wang resin (S. S. Wang, *J. Amer. Chem. Soc.* 95: 1328, 1973) in 130 mL of dry solvent (the resin should be swollen in the appropriate solvent for a minimum of 2 hours prior to coupling; the choice of solvent is dictated by the solubility of the carboxyaldehyde linker). The solvent can be dichloromethane, tetrahydrofuran, or N,N-dimethylformamide (DMF). To this mixture is added 18 mmol of the appropriate carboxyaldehyde (3 equiv), 18 mmol (3 equiv.) of dicyclohexylcarbodiimide (DCC) or diisopropylcarbodiimide (DIC) and 6 mmol (1 equiv.) of 4-dimethylaminopyridine. The mixture is magnetically stirred for 48 hours at ambient temperatures. The supernatant is then filtered off and the resin thoroughly washed with DMF (500 mL), methanol (500 mL), dichloromethane (500 mL), and methanol (500 mL). The polymer is dried in vacuo (0.1 mmHg) for 24 hours. Coupling yields are determined by cleaving 100 mg of the resin with a solution of 20% trifluoroacetic acid in dichloromethane for 20 minutes at ambient temperatures. In case of low coupling yields (<70%), the procedure can be repeated.

The carboxyaldehyde may also be coupled to Tentagel PHB resin (E. Bayer, *Angew. Chem. Int. Ed. Engl.* 30: 113–129, 1991) as the solid support in place of Wang resin. A typical procedure involves reacting 0.24 mmol (1 equiv) of Tentagel PHB resin in 13 mL of dry solvent (the resin should be swollen in the appropriate solvent for a minimum of 2 hours prior to coupling; the choice of solvent is dictated by the solubility of the carboxyaldehyde linker). The solvent can be dichloromethane, tetrahydrofuran, or N,N-dimethylformamide. To this mixture is added 1.2 mmol (5 equiv) of the appropriate carboxyaldehyde, 1.2 mmol (5 equiv) of diisopropylcarbodiimide, and 0.24 mmol of 4-dimethylaminopyridine. The mixture is stirred magnetically for 24 hours at ambient temperatures. The supernatant is then filtered off and the resin thoroughly washed with DMF (100 mL), methanol (100 mL), dichloromethane (100 mL), and methanol (100 mL). The polymer is dried in vacuo (0.1 mmHg) for 24 hours. Coupling yields are determined by cleaving 100 mg of the resin with a solution of 20% trifluoroacetic acid in dichloromethane for 20 minutes at ambient temperatures.

Examples of carboxyaldehyde linkers used in the generation of resins and coupling yields are as follows:

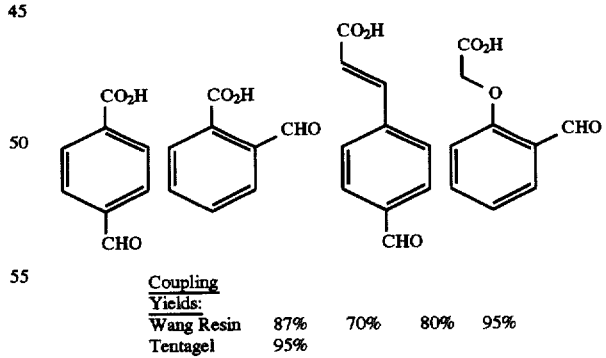

| Coupling Yields: | | | | |
|---|---|---|---|---|
| Wang Resin | 87% | 70% | 80% | 95% |
| Tentagel | 95% | | | |

The synthesis of the alkoxyaldehyde resin of general formula 3 is shown in Scheme 3 and employs methodologies described by Richter and Gadek, *Tetrahedron Lett.* 35:4705 (1994). A typical procedure involves reacting 1 mmol (1 equiv.) of Wang resin in 4-ethylmorpholine (5 mL) with 3 mmol (3 equiv.) of the appropriate alkoxyaldehyde in the presence of 3 mmol (3 equiv.) of triphenylphosphine. The flask is cooled to 0° C. and 3 mmol (3 equiv.) of di-isopropyl azodicarboxylate (DIAD) is added dropwise to the mixture. The reaction is placed in a sonicator bath for 1 hour at 23° C. Following sonication, the mixture is magnetically stirred for 16 hours at ambient temperatures. The supernatant is then filtered off and the resin thoroughly washed with acetic acid (50 mL), methanol (50 mL), dichloromethane (50 mL), and methanol (50 mL). The polymer is then dried in vacuo (0.1 mmHg) for 24 hours. Coupling yields are determined by cleaving 100 mg of the resin with a solution of 20% trifluoroacetic acid in dichloromethane for 20 minutes at ambient temperatures. In case of low coupling yields (<70%), the procedure can be repeated.

SCHEME 3

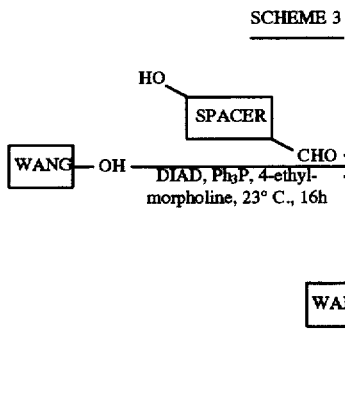

Examples of alkoxyaldehyde linkers used in the generation of resins and coupling yields are as follows:

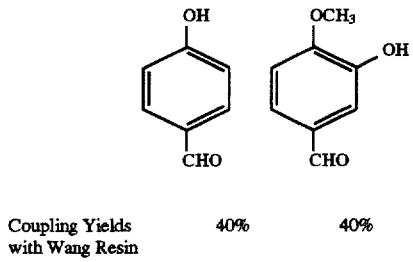

The solid-phase method using a FMOC-amino acid linker (Scheme 4) involves synthesis of the substituted imidazoles by reaction of the 1,2-ethanediones of general formula 1 with the aldehydes of general formula 2 and the amine-linked resin of general formula 3 in the presence of ammonium acetate followed by treatment with 20% trifluoroacetic acid in dichloromethane to afford the substituted imidazole compounds of general formula 4.

SCHEME 4

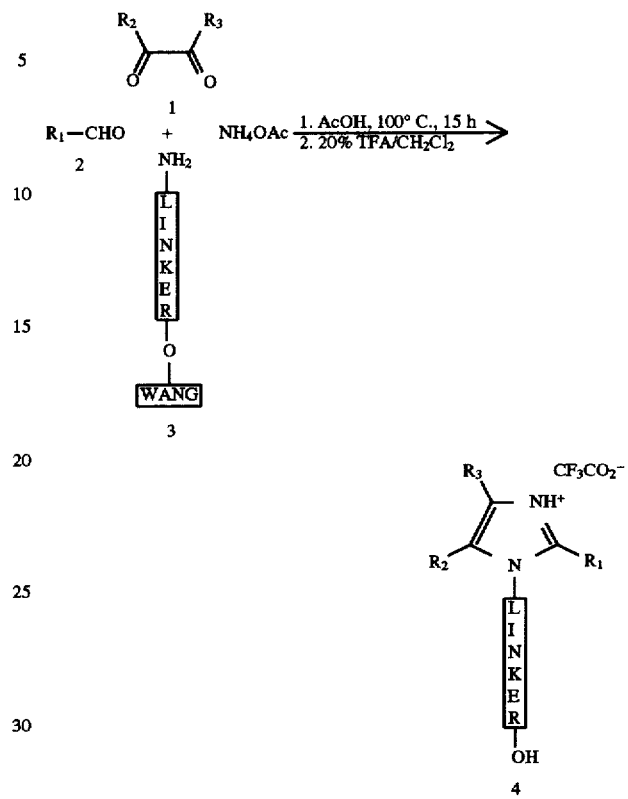

The synthesis of the FMOC-amino acid linker of general formula 3 is shown in Scheme 5 and employs methodologies described by G. B. Fields and R. L. Noble, *Int. J. Peptide Res.* 35:161 (1990) and references cited therein. A typical procedure involves reacting 3 mmol (1 equiv) of Wang resin in dry dichloromethane (92 mL) (the resin should be swollen in dichloromethane for a minimum of 2 hours prior to coupling) with 9 mmol (3 equiv) of the Fmoc-amino acid in the presence of 9 mmol (3 equiv) of DCC or DIC and 3 mmol (1 equiv) of 4-dimethylaminopyridine. The mixture is stirred magnetically for 48 hours at ambient temperatures. The supernatant is then filtered off and the resin thoroughly washed with DMF (500 mL), methanol (500 mL), water (500 mL), methanol (500 mL), dichloromethane (500 mL), and methanol (500 mL). The polymer is dried in vacuo (0.1 mmHg) for 24 hours. Coupling yields are determined by cleaving 100 mg of the resin with a solution of 20% trifluoroacetic acid in dichloromethane for 20 minutes at ambient temperatures. In case of low coupling yields (<70%), the procedure can be repeated.

SCHEME 5

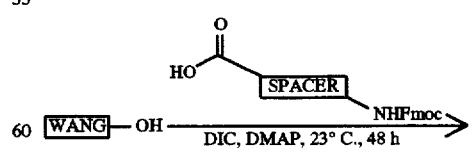

-continued
SCHEME 5

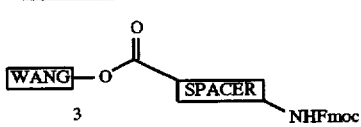

An example of an Fmoc-amino acid linker and coupling yield is as follows:

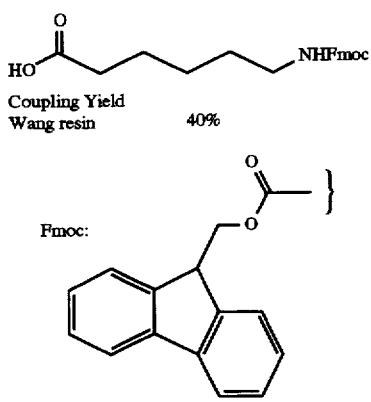

Coupling Yield
Wang resin  40%

The solution-phase methods for preparing the imidazoles of the present invention are shown in Schemes 6 and 7. The synthesis of the (1H)-imidazole derivatives is shown in Scheme 6 and involves reaction of the 1,2-ethanediones of general formula 1 with aldehydes of general formula 2 in the presence of ammonium acetate in acetic acid at 100° C. to afford (1H)-imidazoles of general formula 3.

SCHEME 6

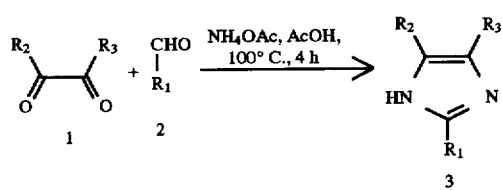

The synthesis of the N-substituted imidazole derivatives in solution phase is shown in Scheme 7 and involves reaction of the 1,2-ethanediones of general formula 1 with aldehydes of general formula 2 and primary amines of general formula 4 in the presence of ammonium acetate in acetic acid at 100° C. to afford N-substituted imidazoles of general formula 3.

SCHEME 7

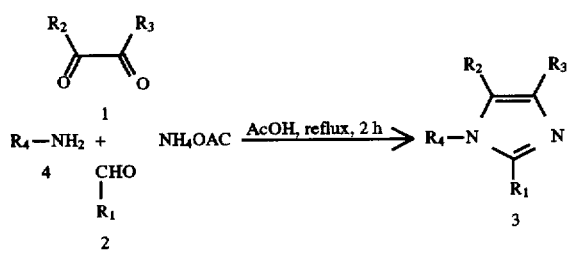

The compounds described herein are capable of sensitizing multi-drug resistant tumor cells to antitumor chemotherapeutic agents, such as doxorubicin and vinblastine. They also have the ability to potentiate the sensitivity of tumor cells susceptible to these chemotherapeutic agents.

This invention also relates to a method of sensitizing multidrug-resistant tumor cells to antitumor chemotherapeutic agents. It also relates to a method of increasing the sensitivity of drug-susceptible tumor cells to antitumor chemotherapeutic agents. In addition, this invention relates to a method of preventing the emergence of MDR tumor cells during a course of treatment with antitumor chemotherapeutic agents. Finally, this invention relates to a method of reducing the effective dosage of an antitumor chemotherapeutic agent during a course of treatment. It has been found that compounds of Formula I have the ability to increase the sensitivity of MDR mammalian cells in culture.

Cytotoxic drugs are commonly used as antitumor chemotherapeutic agents. These agents are also called antiproliferative agents. The desired effect of cytotoxic drugs is selective cell death with destruction of the malignant neoplastic cells and relative sparing of normal cells.

Cytotoxic drugs have also proved valuable in the treatment of other neoplastic disorders including connective or autoimmune diseases, metabolic disorders, dermatological diseases, and DNA virus infections.

Proper use of cytotoxic drugs requires a thorough familiarity with the natural history and pathophysiology of the disease before selecting the cytotoxic agent, determining a dose, and undertaking therapy. Each patient must be carefully evaluated, with attention directed toward factors which may potentiate toxicity, such as overt or occult infections, bleeding dyscrasias, poor nutritional status, and severe metabolic disturbances. In addition, the functional condition of certain major organs, such as liver, kidneys, and bone marrow, is extremely important. Therefore, the selection of the appropriate cytotoxic agent and devising an effective therapeutic regimen is influenced by the presentation of the patient.

Cytotoxic drugs as antitumor chemotherapeutic agents can be subdivided into several broad categories, including, (1) alkylating agents, such as mechlorethamine, cyclophosphamide, melphalan, uracil mustard, chlorambucil, busulfan, carmustine, lomustine, semustine, streptozoticin, and decrabazine; (2) antimetabolites, such as methotrexate, fluorouracil, fluorodeoxyuridine, cytarabine, azarabine, idoxuridine, mercaptopurine, azathiopfine, thioguanine, and adenine arabinoside; (3) natural product derivatives, such as vinblastine, vincristine, dactinomycin, daunorubicin, doxorubicin, mithramycin, bleomycin, etoposide, teniposide, and mitomycin-C; and (4) miscellaneous agents, such as hydroxyurea, procarbezine, mititane, and cis-platinum.

Important antitumor chemotherapeutic agents (with the usual effective dosage) to which clinical multidrug-resistance has been observed include vinblastine (0.1 mg per kilogram per week), vincristine (0.01 mg per kilogram per week), etoposide (35 to 50 mg per square meter per day), dactinomycin (0.15 mg per kilogram per day), doxorubicin (500 to 600 mg per square meter), daunorubicin (65 to 75 mg per square meter per week), and mithramycin (0.025 mg per kilogram per day). MDR has been shown to occur in vitro as well as in the clinic.

Multidrug-resistant cell lines are easily obtainable for in vitro determination of drug sensitization by compounds of the present invention. In vitro potentiation of antineoplastic cytotoxicity by the imidazole derivatives of the present invention was measured in both CEM/VLB1000 and SK/VLB1000 cell lines. The multidrug resistant cell lines were obtained from Dr. Victor Ling, Ontario Cancer Institute, Toronto, Canada. The CEM/VLB 1000 cell line was maintained as a suspension in minimum essential medium supplemented with 10% of fetal bovine serum in a humidied atmosphere of 95% air and 5% $CO_2$ while the SK/VLB 1000 cell 20 line was maintained as adherent cells using the identical medium conditions as the CEM cells. The CEM/VLB 1000 cells were seeded at a density of $5 \times 10^4$ cells/well in a 96 well microtiter plate while the SK/VLB 1000 cell line was seeded at a density of 2,500 cells/well after trypsinization. Vinblastine (5 μg/mL, for the CEM cells) or Taxel (3 μg/mL, for the SK cells) and compound (0.01 to 50 μM) were added directly to the wells. After an incubation of 48 hours in presence of drug, alamar blue (B. Page et al., Int. J. Oncol. 3: 473–476, 1993) was added (20 μL to the 200 μL cell suspension) for a period of 24 hours after which the fluorescence (excitation=530 nM, emission= 590 nM) was read for each well using a "CytoFluor" microtiter fluorometer plate reader. This assay measures the minimal concentration of compound necessary to enhance the cytotoxicity ($EC_{50}$) of vinblastine in the MDR cell line. The compounds of the present invention had $EC_{50}$ values in the range of 0.3 to 10 μM.

Enhancement of $^3$H-vinblastine accumulation was also measured in the cell line. Corning Easy-Wash 96 well plates were pretreated with PBS and 1% BSA for 60 minutes and then dried. CEM/VLB 1000 cells were seeded at $2 \times 10^5$, 40 μL volume. Plates were incubated at 37° C. for 30–60 minutes prior to use. The reference reversing agent, verapamil, or the compound of the present invention was added to the well followed by addition of media containing 3H-vinblastine (final concentration=550 nM). Plates were allowed to incubate for 3 hours at 37° C. Cells were harvested onto pretreated Wallace filtermats B (pretreated overnight with 0.1% polyethyleneimine) using a TomTek harvester-96. After filtering, the filtermats were allowed to dry completely. Meltix B scintillant was then added to the filtermats. The filters were then placed in a 90° C. oven for approximately 3–5 minutes and then removed. Scintillant was allowed to solidify on the filtermats. Filtermats were then placed in sample bags and read on a Wallace BetaPlate scintillation counter. The effect of compounds of the present invention in the cytotoxicity potentiation assays and vinblastine (VLB) accumulation assay is given in the Table below:

| Example | Cytotoxicity Potentiation (μM)[1] | | [$^3$H]VLB Accumulation (μM)[2] |
|---|---|---|---|
| | CEM/VLB1000 Cells | SK/VLB1000 Cells | CEM/VLB1000 Cells |
| 1 | NT[3] | NT | 20 |
| 2 | NT | NT | 2 |
| 3 | 10 | NT | NT |
| 4 | 0.3 | 1.0 | 5.0 |
| 5 | 3.0 | 10 | 12 |
| 6 | 5.0 | NT | NT |
| 7 | 10 | NT | NT |
| 8 | 0.3 | 0.3 | 5.0 |
| 9 | 10 | 10 | 20 |
| 10 | 2.0 | 20 | 10 |
| 11 | 10 | NT | NT |
| 12 | 10 | NT | NT |
| 13 | 0.6 | 20 | NT |
| 14 | 0.4 | 1 | NT |
| 15 | 0.6 | 5 | NT |
| 16 | 2.0 | 10 | NT |
| 17 | 20 | 20 | NT |

[1]Values presented are the midpoint ($EC_{50}$) of the minimum and maximum cytotoxicity induced by 5 μg/mL vinblastine and the specific compound of the present invention.
[2]Values presented are the midpoint ($EC_{50}$) of the minimum and maximum increase in accumulation of $^3$H-vinblastine caused by the specific compound of the present invention.
[3]NT = Not tested.

The modulation of multidrug-resistance demonstrated by the imidazole derivatives described herein provides a method of treatment of multidrug-resistant tumors. The multidrug-resistance modulatory properties of the compounds described herein also provides a method for the prevention of the emergence of multi-drug resistant tumors during the course of cancer treatment. These same compounds additionally provide a method for reducing the required dosage of an antitumor chemotherapeutic agent.

All of the methods of this invention involve (1) the administration of a compound of Formula 1 prior to, together with, or subsequent to the administration of an antitumor chemotherapeutic agent; and (2) the administration of a combination of a compound of Formula 1 and an antitumor chemotherapeutic agent.

Thus, the compounds of Formula 1 are useful in the treatment of multidrug-resistant tumor cells or tumor cells in general, either separately or in combination with an antitumor chemotherapeutic agent. These compounds may be administered orally, topically or parenterally in dosage unit formulations containing conventional non-toxic pharmaceutically acceptable carriers, adjuvants, and vehicles. The term parenteral as used herein includes subcutaneous injections, intravenous, intramuscular, intrasternal injection or infusion techniques.

The present invention also has the objective of providing suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. The tablets contain the acting ingredient in admixture with non-toxic pharmaceutically acceptable excipients which are suitable for the manufacture of tablets. These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such expicients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

A compound of Formula 1 may also be administered in the form of suppositories for rectal administration of the drug. These compositions can be prepared by mixing the drug with a suitable non-irritating excipient which is solid at ordinary temperature but liquid at the rectal temperature and will therefore melt in the rectum to release the drug. Such materials are cocoa butter and polyethylene glycols.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For topical use, creams, ointments, jellies, solutions or suspensions, etc., containing the compounds of Formula 1 are employed.

Dosage levels of the compounds of the present invention are of the order of about 0.5 mg to about 100 mg per kilogram body weight, with a preferred dosage range between about 20 mg to about 50 mg per kilogram body weight per day(from about 25 mg to about 5 gms per patient per day). The amount of active ingredient that may be combined with the carrier materials to produce a single dosage will vary depending upon the host treated and the particular mode of administration. For example, a formulation intended for oral administration to humans may contain 5 mg to 1 g of an active compound with an appropriate and convenient amount of carrier material which may vary from about 5 to about 95 percent of the total composition. Dosage unit forms will generally contain between from about 5 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to illustrate the preparation of compounds of Formula 1, and as such are not intended to limit the invention as set forth in the claims appended thereto. Furthermore, the compounds described in the following examples are not to be construed as forming the only genus that is considered as the invention, and any combination of the compounds or their moieties may itself form a genus. The structure and purity of all final products were assured by at least one of the following methods: thin-layer chromatography (TLC), mass spectroscopy, nuclear magnetic resonance (NMR) spectroscopy, or combustion analysis. NMR data is in the form of delta (d) values for major diagnostic protons, given in parts per million (ppm) relative to tetramethylsilane (TMS) as internal standard, determined at 400 MHz in deuteriochloroform ($CDCl_3$); conventional abbreviations used for signal shape are: s, singlet; d, doublet; t, triplet; m, multiplet; br., broad; etc. The following abbreviations have also been used: v (volume), w (weight), L (liter), mL (milliliter), g (gram), mg (milligram), mol (moles), mmol (millimoles), equiv (equivalents).

The Examples were prepared using either Method A or Method B.

Method A involves synthesis on a solid support either with aldehyde linkers as shown in Scheme 1 above or FMOC-amino acid linkers as shown in Scheme 4 above.

In a typical Method A procedure using an aldehyde linker, to 0.1 mmol (1 equiv.) of the carboxyaldehyde resin or alkoxyaldehyde resin was added 1 mmol (1 equiv.) of 1,2-diarylethanedione, 1 mmol (10 equiv.) of the amine ($R_4NH_2$), 0.14 mmol (1.4 equiv.) of ammonium acetate, and 1.6 mL of acetic acid. The mixture was magnetically stirred for 12 to 15 hours at 100° C. The resin was filtered and washed with dichloromethane (40 mL), N,N-dimethylformamide (20 mL), methanol (20 mL), dichloromethane (40 mL), and methanol (40 mL). The product was cleaved from the resin with a solution of 20% trifluoroacetic acid in dichloromethane for 20 minutes at ambient temperatures. The substituted imidazoles were purified using reverse-phase HPLC Rainin Dynamax C18 columns and mixtures of water and acetonitrile containing 0.1% trifluoroacetic acid as the mobile phase.

In a typical Method A procedure using a FMOC-amino acid linker, 0.1 mmol (1 equiv.) of the FMOC-amino acid resin was deprotected using 20% piperidine in DMF (10 mL) at ambient temperatures for 20 minutes. The resin was washed with DMF (10 mL), dichloromethane (2×20 mL), methanol (2×20 mL), and acetic acid (2×20 mL). To the deprotected resin was added 1 mmol (10 equiv.) of the 1,2-diarylethanedione, 1 mmol (10 equiv.) of ammonium acetate and 1.6 mL of acetic acid. The mixture was magnetically stirred for 12 to 15 hours at 100° C. The resin was filtered and washed with dichloromethane (40 mL), DMF (20 mL), methanol (20 mL), dichloromethane (40 mL), and methanol (40 mL). The product was cleaved from the resin with a solution of 20% trifluoroacetic acid in dichloromethane for 20 minutes at ambient temperatures. The substituted imidazoles were purified using reverse-phase HPLC Rainin Dynamax C18 columns and mixtures of water and acetonitrile containing 0.1% trifluoroacetic acid as the mobile phase.

Method B involves synthesis of the substituted (1H)-imidazoles in solution phase as shown in Scheme 6 above. In a typical Method B procedure, 1 mmol (1 equiv.) of the 1,2-ethanedione, 1 mmol (1 equiv.) of the aldehyde, and 20 mmol (20 equiv.) of ammonium acetate in glacial acetic acid (9 mL) were heated to reflux for 4 hours. The extent of the reaction was monitored by thin layer chromatography and nuclear magnetic resonance (NMR) spectroscopy. Once all starting material had disappeared, the solution was cooled to 23° C. and added dropwise to a vigorously stirred mixture of diethyl ether (200 mL) and saturated aqueous sodium hydrogencarbonate (200 mL). Ethyl acetate (200 mL) was added, and the organic layer was separated. The organic layer was washed with saturated aqueous sodium hydrogencarbonate (200 mL) and saturated brine solution (200 mL). The aqueous layers were combined and washed with ethyl acetate (200 mL). The combined organic layers were dried over sodium sulfate, filtered, and solvent removed in vacuo. The derived imidazoles were purified using reverse-phase HPLC Rainin Dynamax C18 columns and mixtures of water and acetonitrile containing 0.1% trifluoroacetic acid as the mobile phase.

Method C involves synthesis of the N-substituted imidazoles in solution phase as shown in Scheme 7 above. In a typical Method C procedure, 2 mmol (1 equiv.) of the 1,2-ethanedione, 2 mmol (1 equiv.) of the aldehyde, 10 mmol (5 equiv) of the primary amine, and 3 mmol (1.5 equiv.) of ammonium acetate in glacial acetic acid (5 mL) were heated to reflux for 2 hours. The extent of the reaction was monitored by thin layer chromatography and nuclear magnetic resonance (NMR) spectroscopy. Once all starting material had disappeared, the solution was cooled to 23° C. and added dropwise to a vigorously stirred mixture of diethyl ether (200 mL) and saturated aqueous sodium hydrogencarbonate (200 mL) or 3.0N sodium hydroxide (200 mL). Ethyl acetate (200 mL) was added, and the organic layer was separated. The organic layer was washed with saturated aqueous sodium hydrogencarbonate (200 mL) or 3.0N sodium hydroxide (200 mL) and saturated brine solution (200 mL). The aqueous layers were combined and washed with ethyl acetate (200 mL). The combined organic layers were dried over sodium sulfate, filtered, and solvent removed in vacuo. The derived N-substituted imidazoles were purified by recrystallization, flash chromatography on Merck F60 silica gel, or reverse-phase HPLC on Rainin Dynamax C18 columns and mixtures of water and acetonitrile containing 0.1% trifluoroacetic acid as the mobile phase.

EXAMPLE 1

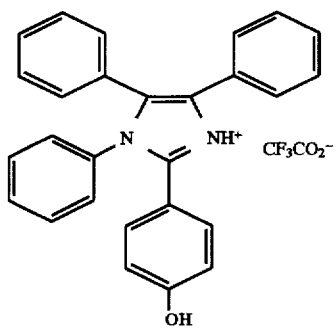

Prepared by method A. $^1$H-NMR: $\delta$(6.6, d, 2H), (7.06, d, 4H), (7.15, d, 2H), (7.2–7.4, m, 11H).

EXAMPLE 2

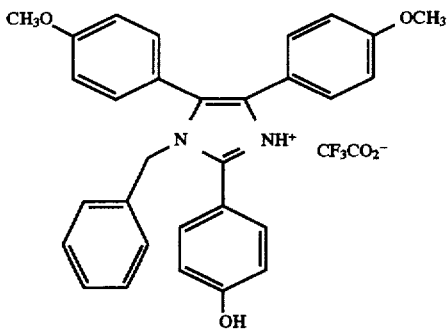

Prepared by method A. $^1$H-NMR: $\delta$(3.7, s, 3H), (3.8, s, 3H), (5.14, s, 2H), (6.7–6.9, m, 9H), (7.09, d, 2H), (7.21, d, 2H), (7.3, d, 2H), (7.4, d, 2H).

EXAMPLE 3

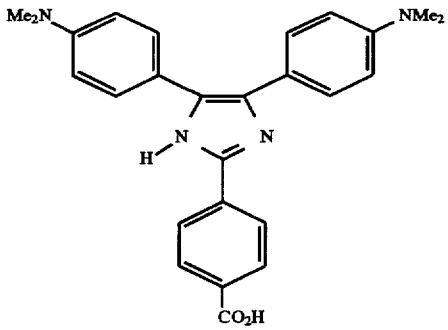

Prepared by method A. 1H-NMR: a (2.9, s, 12H), (6.7, d, 4H), (7.25, d, 4H), (7.95, dd, 4H).

EXAMPLE 4

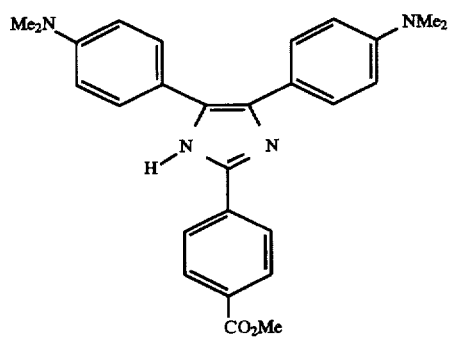

Prepared by method A, followed by reaction with trimethylsilyl-diazomethane in 4:1 methanol-benzene.
$^1$H-NMR: δ(2.9, s, 12H), (4.9, s, 3H), (6.7, d, 4H), (7.4, d, 4H), (7.9, d, 2H), (8.05, d, 2H).

EXAMPLE 5

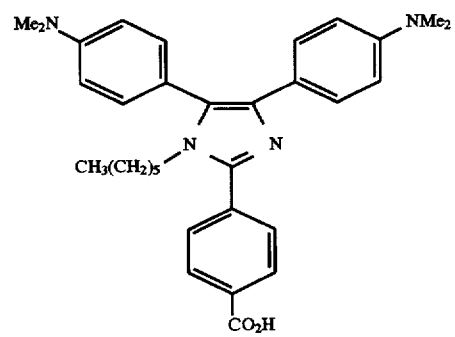

Prepared by method A: $^1$H-NMR: δ(0.6, t, 3H), ), (0.9–1.0, m, 6H), (1.3, m, 2H), (2.8, s, 6H), (3.0, s, 6H), (3.78, dd, 2H), (6.58, d, 2H), (6.72, dd, 4H), (7.19, d, 2H), (7.21, d, 2H), (7.4, d, 2H).

EXAMPLE 6

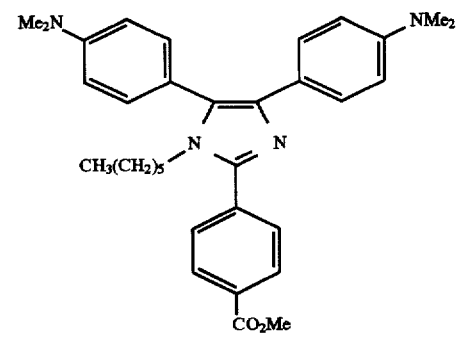

Prepared by method A, followed by reaction with trimethylsilyl-diazomethane in 4:1 methanol-benzene.
$^1$H-NMR: δ(0.6, t, 3H), (0.9–1.0, m, 6H), (1.3, m, 2H), (2.8, s, 6H), (3.0, s, 6H), (3.8, dd, 2H), (3.9, s, 3H), (6.58, d, 2H), (6.78, d, 2H), (7.24, d, 2H), (7.42, d, 2H), (7.78, d, 2H), (8.05, d, 2H).

EXAMPLE 7

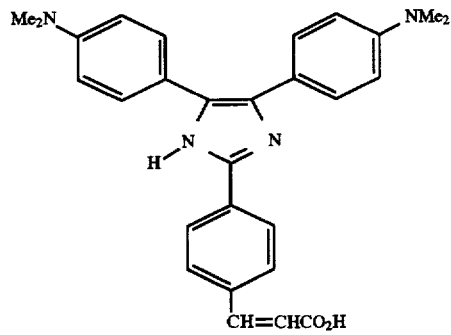

Prepared by method A. $^1$H-NMR: δ(2.9, s, 12H), (6.3, d, 1H), (6.62, d, 4H), (7.4, broad d, 4H), (7.43, d, 2H), (7.6, d, 1H), (7.9, d, 2H).

EXAMPLE 8

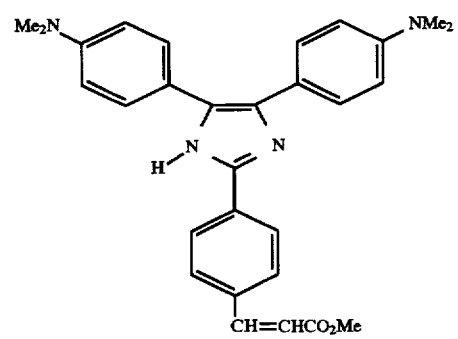

Prepared by method B, followed by reaction with trimethylsilyldiazomethane in 4:1 methanol-benzene. $^1$H-NMR: δ(2.9, s, 12H), (3.78, s, 3H), (6.35, d, 1H), (6.6, d, 4H), (7.38, broad d, 4H), (7.4, d, 2H), (7.6, d, 1H), (7.8, d, 2H).

EXAMPLE 9

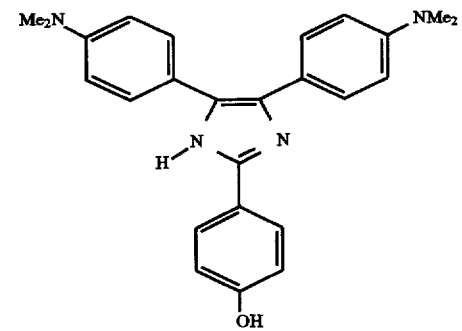

Prepared by method A. $^1$H-NMR: δ(2.9, s, 12H), (6.75, d, 2H), (6.9, d, 4H), (7.3, d, 4H), (7.65, d, 2H).

EXAMPLE 10

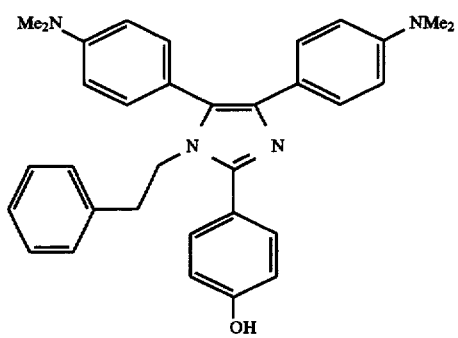

Prepared by method A. ¹H-NMR: δ(2.5, t, 2H), (2.9, s, 6H), (3.0, s, 6H), (4.2, d, 2H), (6.58, d, 2H), (6.72, dd, 2H), (6.9, m, 4H), (7.1, m, 5H), (7.19, d, 2H), (7.25, d, 2H).

EXAMPLE 11

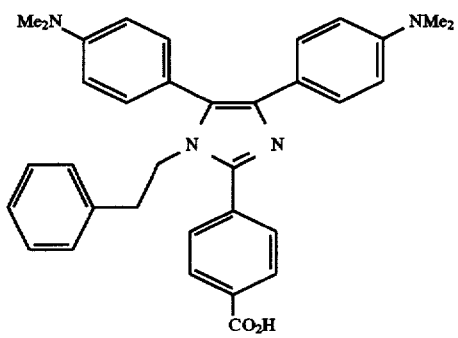

Prepared by method A. ¹H-NMR: δ(2.5, t, 2H), (2.9, s, 6H), (3.0, s, 6H), (4.2, d, 2H), (6.58, d, 2H), (6.72, dd, 2H), (6.9, d, 2H), (7.1, m, 3H), (7.19, d, 2H), (7.35, dd, 4H), (8.05, d, 2H).

EXAMPLE 12

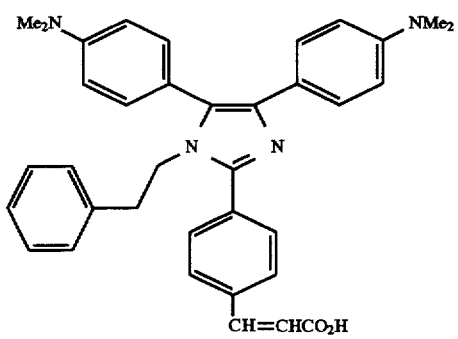

Prepared by method A. ¹H-NMR: δ(2.5, t, 2H), (2.9, s, 6H), (3.0, s, 6H), (4.2, d, 2H), (6.4, d, 1H), (6.5, d, 2H), (6.7, d, 2H), (6.9–7.6, m, 14H).

EXAMPLE 13

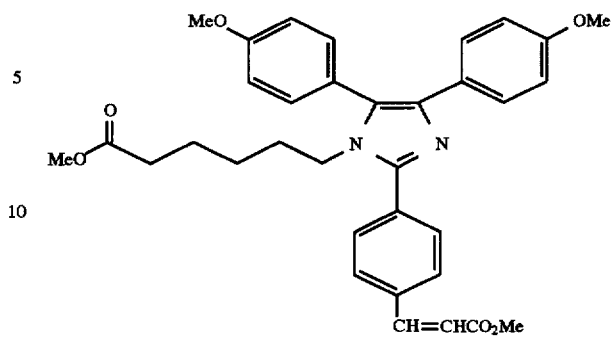

Prepared by method A, followed by reaction with trimethylsilyldiazomethane in 4:1 methanol-benzene. ¹H-NMR: δ(0.9, m, 2H), (1.3, m, 4H), (2.05, t, 2H), (3.55, s, 3H), (3.7, s, 3H), (3.8, s, 3H) (3.85, s, 3H), (3.85, t, 2H), (6.45, d, 1H), (6.7, d, 2H), (6.95, d, 2H), (7.25, d, 2H), (7.4, d, 2H), (7.6, d, 2H), (7.7, d, 2H), (7.7, d, 1H).

EXAMPLE 14

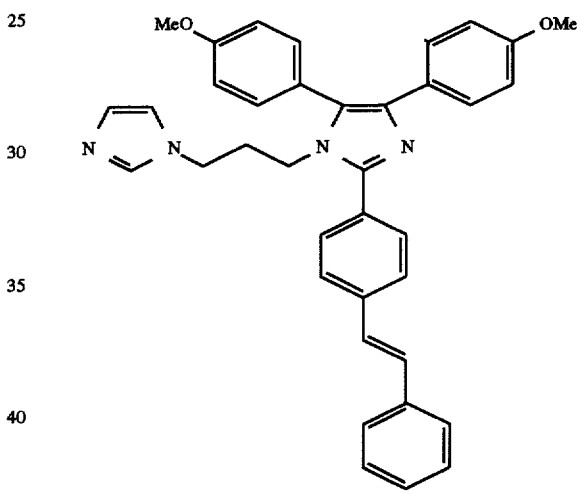

Prepared by method C. ¹H-NMR: δ(1.8, m, 2H), (3.6, t, 2H), (3.7, s, 3H), (3.84, s, 3H), (3.9, t, 2H), (6.42, s, 1H), (6.72, d, 2H), (6.89, s, 1H), (6.98, d, 2H), (7.14, m, 2H), (7.24, m, 3H), (7.35, t, 2H), (7.44, d, 2H), (7.52, d, 2H), (7.58, s, 3H).

EXAMPLE 15

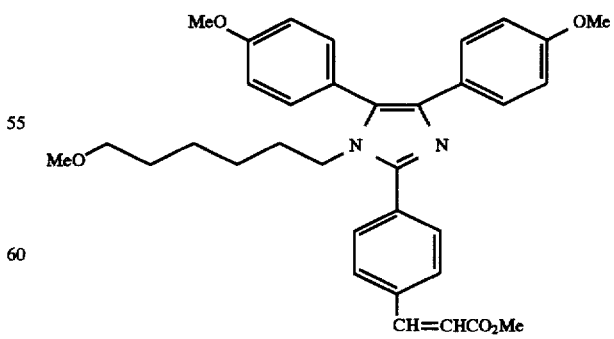

Prepared by method A, followed by reaction with trimethylsilyldiazomethane in 4:1 methanol-benzene. ¹H-NMR: δ(0.9, m, H), (1.3, m, 4H), (2.8, s, 6H), (3.0, s, 6H), (3.58, s, 3H), (3.8, s, 3H), (3.85, t, 2H), (6.45, d, 1H), (6.58, d, 2H), (6.75, d, 2H), (7.2, d, 2H), (7.4, d, 2H), (7.6, d, 2H), (7.7, d, 2H), (7.7, d, 1H).

EXAMPLE 16

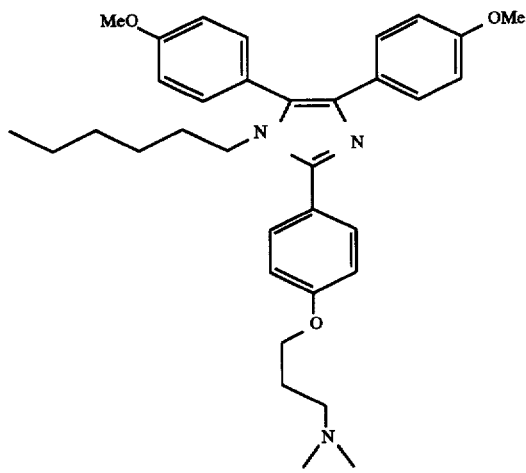

Prepared by method C. $^1$H-NMR: δ(0.7, t, 3H), (0.9, m, 4H), (1.1, m, 2H), (1.3, m, 2H), (1.9, m, 2H), (2.2, s, 6H), (2.45, t, 2H), (3.7, s, 3H), (3.75, t, 2H), (3.84, s, 3H), (4.05, t, 2H), (6.72, d, 2H), (6.98, d, 4H), (7.22, d, 2H), (7.4, d, 2H), (7.52, d, 2H).

EXAMPLE 17

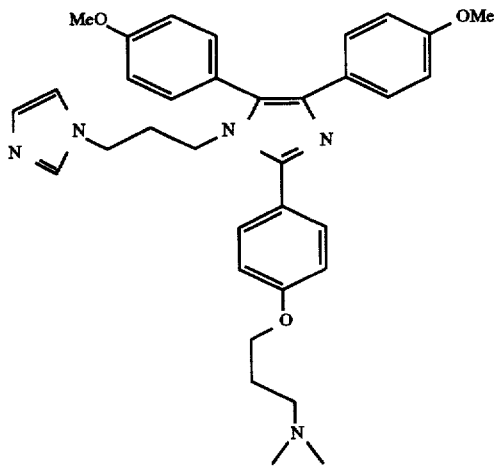

Prepared by method C. $^1$H-NMR: δ(1.7, m, 2H), (1.92, m, 2H), (2.2, s, 6H), (2.4, t, 2H), (3.5, t, 2H), (3.66, s, 3H), (3.78, t, 2H), (3.82, s, 3H), (4.05, t, 2H), (6.42, s, 1H), (6.72, d, 2H), (6.85, s, 1H), (6.91, m, 4H), (7.04, s, 1H), (7.2, d, 2H), (7.41, d, 2H).

What is claimed is:

1. A compound of the formula 1

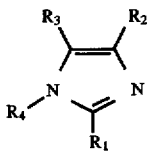

Formula 1 or a pharmaceutically acceptable salt thereof wherein;

$R_1$ is selected from a group consisting of:
(a) substituted $C_{1-11}$ alkyl or substituted $C_{2-11}$ alkenyl, wherein the substituent is selected from the group consisting of hydroxy, $C_{1-6}$ alkyloxy, or
(b) mono-, di-,and tri-substituted aryl-$C_{0-11}$ n alkyl, wherein aryl is selected from the group consisting of phenyl, furyl, thienyl, the substituents are selected from the group consisting of:
(d) phenyl, trans-2-phenylethenyl, 2-phenylethynyl, 2-phenylethyl, or in which the said phenyl group is mono- or disubstituted with a member selected from the group consisting of hydroxy, halo, $C_{1-4}$ alkyl and alkyloxy.
(g) substituted $C_{1-6}$ alkyl, substituted $C_{2-6}$ alkyloxy, substituted $C_{2-6}$alkylthio, substituted substituted $C_{2-6}$alkylcarbonyl, wherein the substituent is selected from the group consisting of $C_{1-6}$ alkoxy, $C_{1-6}$alkylthio,
(h) $C_{1-11}$ $CO_2R_5$, $C_{1-11}CONHR_5$, trans- $CH=CHCO_2R_5$, or trans-$CH=CHCONHR_5$ wherein $R_5$ is $C_{1-11}$ alkyl, or phenyl $C_{1-11}$ alkyl,
(j) $C_{1-6}$ alkoxycarbonylmethyleneoxy;

$R^2$ and $R_3$ are each independently selected from the group consisting of: furyl mono-, di, and tri-substituted phenyl and furyl wherein the substituents are independently selected from:
(i) halo, trifluoromethyl, $C_{1-6}$ alkyl,
(ii) $C_{1-6}$alkyloxy
(iii) $C_{1-6}$ alkyl-amino, di($C_{1-6}$ alkyl)-amino, with the proviso that at least one of the phenyl and furyl substituents be selected from (ii) or (iii);

and $R_4$ is selected from the a consisting of:
(a) hydrogen;
(b) substituted $C_{1-11}$alkyl or $C_{2-11}$ alkenyl wherein the substituent is independently selected from the group consisting of hydrogen, hydroxy, halo, $C_{1-6}$ alkyloxy, $C_{1-6}$alkylthio, $C_{1-6}$alkylamino, phenyl-$C_{1-6}$ alkylamino, $C_{1-6}$alkoxycarbonyl; or
(c) aryl $C_{0-11}$ alkyl wherein the aryl group is selected from phenyl, imidazolyl, furyl, thienyl.

2. A compound of the formula 1

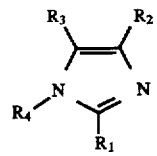

Formula 1 wherein:
$R_1$ is selected from the group consisting of
(a) substituted $C_{1-11}$ alkyl or substituted $C_{2-11}$ alkenyl, wherein the substituents are selected from the group consisting of hydroxy, $C_{1-6}$ alkyloxy; or
(b) mono-, di-, and tri-substituted aryl-$C_{1-10}$ alkyl wherein aryl is selected from the group consisting of phenyl, furyl, thienyl, the substituents are selected from the group consisting of:

phenyl, trans-2-phenylethenyl, 2-phenylethynyl, 2-phenylethyl, or in which the said phenyl group is mono- or disubstituted with a member selected from the group consisting of hydroxy, halo, $C_{1-4}$ alkyl and $C_{2-4}$ alkyloxy.

$R_2$ and $R_3$ are each independently a member selected from the group consisting of furyl and mono- and di-substituted phenyl and furyl wherein the substituents are independently selected from:

(i) halo, trifluoromethyl, $C_{1-6}$ alkyl, (ii) $C_{1-6}$ alkyloxy, (iii) $C_{1-6}$ alkylamino, and di-($C_{1-6}$ alkyl)-amino;

with the proviso that at least one of the phenyl and furyl substituents be selected from (ii) or (iii), and $R_4$ is selected from the group consisting of:

(a) hydrogen;

(b) substituted $C_{1-11}$ alkyl or $C_{2-11}$ alkenyl wherein the substituents are independently selected from the group consisting of hydrogen, hydroxy, halo, $C_{1-6}$ alkyloxy, $C_{1-6}$ alkylthio, $C_{1-6}$ alkylamino, phenyl-$C_{1-6}$ alkylamino, $C_{1-6}$ alkoxycarbonyl; or (c) aryl $C_{0-11}$ alkyl wherein the aryl group is selected from phenyl, imidazolyl, furyl, thienyl.

3. A compound of the formula 1

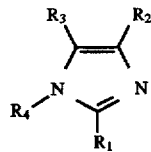

Formula 1 wherein:

$R_1$ is selected from the group consisting of:

(a) substituted $C_{1-11}$ alkyl or substituted $C_{2-11}$ alkenyl, wherein the substituents are selected from the group consisting of hydroxy, $C_{1-6}$ alkyloxy: or (b) mono-, di-, and tri-substituted aryl-$C_{0-11}$ alkyl wherein aryl is selected from the group consisting of phenyl, furyl, thienyl, the substituents are selected from the group consisting of:

substituted $C_{1-6}$ alkyl, substituted $C_{2-6}$ alkyloxy, substituted $C_{2-6}$ alkylthio, substituted $C_{2-6}$ alkoxycarbonyl, wherein the substituents are selected from the group consisting of $C_{1-6}$ alkoxy, $C_{1-6}$ alkylthio, $R_2$ and $R_3$ are each independently selected from the group consisting of furyl, mono-, di, and tri-substituted phenyl and furyl wherein the substituents are independently selected from:

(i) halo, trifluoromethyl, $C_{1-6}$ alkyl, (ii) $C_{1-6}$ alkyloxy, (iii) $C_{1-6}$ alkyl-amino, di($C_{1-6}$ alkyl)amino, with the proviso that at least one of the phenyl and furyl substituents be selected from (ii) or (iii), and $R_4$ is selected from the group consisting of:

(a) hydrogen;

(b) substituted $C_{1-11}$ alkyl or $C_{2-11}$ alkenyl wherein the substituents are independently selected from the group consisting of hydrogen, hydroxy, halo, $C_{1-6}$ alkyloxy, $C_{1-6}$ alkylthio, $C_{1-6}$ alkylamino, phenyl-$C_{1-6}$ alkylamino, $C_{1-6}$ alkoxycarbonyl; or (c) aryl $C_{0-11}$ alkyl wherein the aryl group is selected from phenyl, imidazolyl, furyl, thienyl.

4. A compound of the formula 1

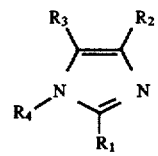

Formula 1 wherein:

$R_1$ is selected from the group consisting of: mono- substituted aryl-$C_{0-11}$ alkyl wherein aryl is selected from the group consisting of phenyl, the substituents are selected from the group consisting of:

$C_{1-4}$ alkyl and $C_{2-4}$ alkyloxy, $C_{1-6}CO_2R_5$, trans-CH=CHCO$_2$R$_5$, wherein $R_5$ is $C_{1-6}$alkyl, or phenyl $C_{1-6}$ alkyl, $R_2$ and $R_3$ are each independently selected from the group consisting of, mono substituted phenyl wherein the substituents are independently selected from:

$C_{1-6}$ alkyloxy and $R_4$ is selected from the group consisting of:

$C_{1-6}$ alkyloxy, $C_{1-6}$alkylamino, or aryl $C_{0-6}$ alkyl wherein the aryl group is selected from phenyl, imidazol and the pharmaceutically acceptable salts thereof.

5. A compound according to formula 1 wherein $R_1$ is 4-hydroxyphenyl; $R_2$ and $R_3$ are methoxyphenyl; and $R_4$ is benzyl; or the pharmaceutically acceptable salts thereof.

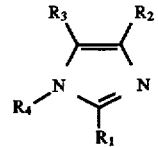

Formula 1

6. A compound according to formula 1 wherein $R_1$ is 4-carboxyphenyl; $R_2$ and $R_3$ are 4-(dimethylamino)-phenyl; and $R_4$ is benzyl or the pharmaceutically acceptable salts, thereof.

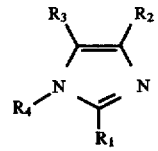

Formula 1

7. A compound according to Formula 1 wherein $R_1$ is 4-methoxy carbonyl; $R_2$ and $R_3$ are 4-(dimethyamino)-phenyl; and $R_4$ is hydrogen or the pharmaceutically acceptable salts thereof.

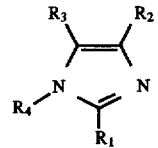

Formula 1

8. A compound according to Formula 1 those compounds wherein $R_1$ is 4-carboxyphenyl; $R_2$ and $R_3$ are (dimethylamino)-phenyl: and $R_4$ is n-hexyl; the pharmaceutically acceptable salts thereof.

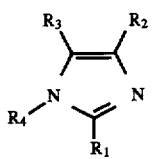

9. A compound according to formula 1 those compounds wherein $R_1$ is 4-(methoxycarbonyl)-phenyl; $R_2$ and $R_3$ are (dimethylamino)-phenyl; and $R_4$ is n-hexyl; the pharmaceutically acceptable salts, thereof.

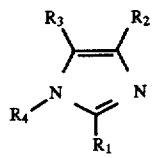

10. A compound according to formula 1 those compounds wherein $R_1$ is 4-carboxyethenyl)-phenyl; $R_2$ and $R_3$ are (dimethylamino)-phenyl; and $R_4$ is hydrogen; the pharmaceutically acceptable salts, thereof.

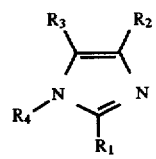

11. A compound according to formula 1 those compounds wherein $R_1$ is 4-(methoxycarbonyl)-phenyl; and $R_2$ and $R_3$ are (dimethylamino)-phenyl; and $R_4$ is n-hexyl; the pharmaceutically acceptable salts, thereof.

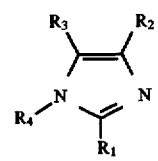

12. A compound according to formula 1 those compounds wherein $R_1$ is 4-hydroxyphenyl; $R_2$ and $R_3$ are -(dimethylamino)-phenyl; and $R_4$ is hydrogen; or the pharmaceutically acceptable salts, thereof.

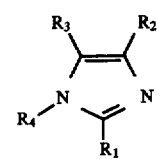

13. A compound according to formula 1 those compounds wherein $R_1$ is 4-hydroxyphenyl; $R_2$ and $R_3$ are -(dimethylamino)-phenyl; and $R_4$ is -phenylethyl; or the pharmaceutically acceptable salts thereof.

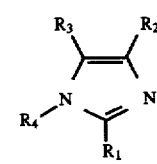

14. A compound according to formula 1 those compounds wherein $R_1$ is 4-carboxyphenyl; $R_2$ and $R_3$ are -(dimethylamino)-phenyl; and $R_4$ is -phenylethyl; or the pharmaceutically acceptable salts, thereof.

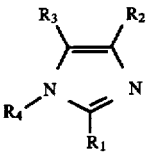

15. A compound according to formula 1 those compounds wherein $R_1$ is 4-(trans-2-carboxyethenyl)-phenyl; $R_2$ and $R_3$ are -(dimethylamino)-phenyl; and $R_4$ is -phenylethyl; or the pharmaceutically acceptable salts thereof.

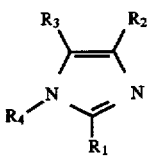

16. A compound according to formula 1 those compounds wherein $R_1$ is 4-phenyl; $R_2$ and $R_3$ are 4-methoxyphenyl; and $R_4$ is 5-(methoxycarbonyl)-n-pentyl; or the pharmaceutically acceptable salts thereof.

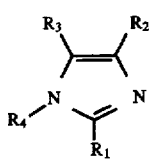

17. A compound according to formula 1 those compounds wherein $R_1$ is trans-4-stilbenyl; $R_2$ and $R_3$ are 4-methoxyphenyl; and $R_4$ is 3-(imidazol-1-yl)-n-propyl; or the pharmaceutically acceptable salts thereof.

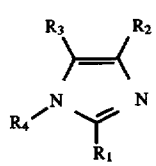

18. A compound according to formula 1 those compounds wherein $R_1$ is 4-phenyl; $R_2$ and $R_3$ are 4-(dimethylamino)-phenyl; and $R_4$ is 5-(methoxycarbonyl)-n-pentyl; or the pharmaceutically acceptable salts thereof,

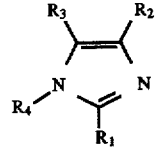

19. A compound according to formula 1 those compounds wherein $R_1$ is 4-phenyl; $R_2$ and $R_3$ are 4-methoxyphenyl; and $R_4$ is 3(imidazol-1-yl)-n-propyl; or the pharmaceutically acceptable salts thereof.

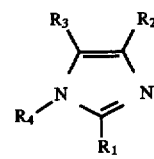

20. A compound according to formula 1 those compounds wherein $R_1$ is 4-phenyl; $R_2$ and $R_3$ are 4-methoxyphenyl; and $R_4$ is n-hexyl; or the pharmaceutically acceptable salts, thereof.

21. A method of treatment for increasing the sensitivity of tumor cells to anti-cancer chemotherapeutic agents, said tumor cells being susceptible to anticancer chemotherapeutic agents, and said tumor cells having become resistant to chemotherapy comprising administration to a mammalian species in need of such treatment a therapeutically effective amount of a compound of claim 1 and a pharmaceutically acceptable carrier.

22. A method of treatment of tumor cells, said tumor cells being susceptible to anti-cancer chemotherapeutic agents, and said tumor cells having become resistant to chemotherapy comprising: administration to a mammalian species in need of such treatment, of a therapeutically effective amount of said anti-cancer chemotherapeutic agent, and an effective amount of a compound of claim 1.

23. A method of treatment of tumor cells according to claim 20, comprising: administration to a mammalian species in need of such treatment a therapeutically effective amount of an anti-cancer chemotherapeutic agent selected from the group consisting of taxol, vinblastine, vincristine, daunorubicin, and doxorubicin.

24. A pharmaceutical composition for increasing the sensitivity of tumor cells to anti-cancer chemotherapeutic agents, said tumors cells having become resistant to chemotherapy comprising a therapeutically effective amount of a compound of claim 1 and a pharmaceutically acceptable carrier.

25. A pharmaceutical composition for increasing the sensitivity of tumor cells to anti-cancer chemotherapeutic agents, said tumors cells having become resistant to chemotherapy comprising: a therapeutically effective amount of an anti-cancer chemotherapeutic agent selected from the group consisting of taxol, vinblastine, vincristine, daunorubicin, and doxorubicin, an effective amount of a compound of claim 1, and a pharmaceutically acceptable carrier.

26. A compound of the formula 1

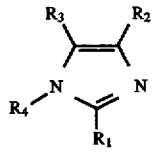

Formula 1 wherein:
$R_1$ is selected from the group consisting of:
- (a) substituted $C_{1-11}$ alkyl or substituted $C_{2-11}$ alkenyl, wherein the substituents are selected from the group consisting of hydroxy, $C_{1-6}$ alkyloxy: or
- (b) mono-,di-,and tri-substituted aryl-$C_{0-11}$ alkyl wherein aryl is selected from the group consisting of phenyl, furyl, thienyl, the substituents are selected from the group consisting of:
  $C_{1-11}$ $CO_2R_5$, $C_{1-11}CONHR_5$, trans-CH=CHCO$_2$R$_5$, or trans-CH=CHCONHR$_5$ wherein $R_5$ is $C_{1-11}$ alkyl, or phenyl $C_{1-11}$ alkyl, $C_{1-6}$ alkoxycarbonylimethyleneoxy.

$R_2$ and $R_3$ are each independently selected from the group consisting of furyl, mono-, di, and tri-substituted phenyl and furyl wherein the substituents are independently selected from:
  (i) halo, trifluoromethyl, $C_{1-6}$ alkyl,
  (ii) $C_{1-6}$ alkyloxy,
  (iii) $C_{1-6}$alkyl-amino, di($C_{1-6}$ alkyl)amino,
with the proviso that at least one of the phenyl and furyl substituents be selected from (ii) or (iii).
and $R_4$ is selected from the group consisting of:
- (a) hydrogen;
- (b) substituted $C_{1-11}$ alkyl or $C_{2-11}$ alkenyl wherein the substituents are independently selected from the group consisting of hydrogen, hydroxy, halo, $C_{1-6}$ alkyloxy, $C_{1-6}$alkylthio, $C_{1-6}$alkylamino, phenyl-$C_{1-6}$-alkylamino, $C_{1-6}$alkoxycarbonyl; or
- (c) aryl $C_{0-11}$ alkyl wherein the aryl group is selected from phenyl, imidazolyl, furyl, or thienyl; or the pharmaceutically acceptable salts thereof.

27. A compound of the formula 1

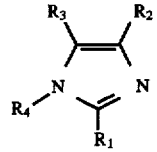

Formula 1 wherein:
$R_1$ is selected from the group consisting of:
- (a) substituted $C_{1-11}$ alkyl or substituted $C_{2-11}$ alkenyl, wherein the substituents are selected from the group consisting of hydroxy, $C_{1-6}$ alkyloxy: or
- (b) mono-,di-,and tri-substituted aryl-$C_{0-11}$ alkyl wherein aryl is selected from the group consisting of phenyl, furyl, thienyl, the substituents are selected from the group consisting of:
  phenyl, trans-2-phenylethenyl, 2-phenylethynyl, 2-phenylethyl, or in which the said phenyl group is mono- or disubstituted with a member selected from the group consisting of hydroxy, halo, $C_{1-4}$ alkyl and $C_{2-4}$alkyloxy, $R_2$ and $R_3$ are each independently selected from the group consisting of furyl, mono-, di, and tri-substituted phenyl and furyl wherein the substituents are independently selected from:
  (i) halo, trifluoromethyl, $C_{1-6}$ alkyl,
  (ii) $C_{1-6}$ alkyloxy,
  (iii) $C_{1-6}$ alkyl-amino, di($C_{1-6}$ alkyl)amino,
with the proviso that at least one of the phenyl and furyl substituents be selected from (ii) or (iii).
and R, is selected from the group consisting of:
- (a) hydrogen;
- (b) aryl $C_{0-11}$ alkyl wherein the aryl group is selected from phenyl, imidazolyl, furyl, or thienyl; or the pharmaceutically acceptable salts thereof.

28. A compound of the formula 1

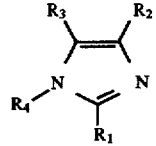

Formula 1 wherein:
$R_1$ is selected from the group consisting of:
- (a) substituted $C_{1-11}$ alkyl or substituted $C_{2-11}$ alkenyl, wherein the substituents are selected from the group consisting of hydroxy, $C_{1-6}$ alkyloxy; or
- (b) mono-,di-,and tri-substituted aryl-$C_{0-11}$ alkyl wherein aryl is selected from the group consisting of phenyl, furyl, thienyl, the substituents are selected from the group consisting of:
  phenyl, trans-2-phenylethenyl, 2-phenylethynyl, 2-phenylethyl, or in which the said phenyl group is mono- or disubstituted with a member selected from the group consisting of hydroxy, halo, $C_{1-4}$ alkyl and $C_{2-4}$ alkyloxy, $R_2$ and $R_3$ are each independently selected from the group consisting of furyl, mono-, di, and tri-substituted phenyl and furyl wherein the substituents are independently selected from:

(i) halo, trifluoromethyl, $C_{1-6}$ alkyl, (ii) $C_{1-6}$ alkyloxy, (iii) $C_{1-6}$ alkyl-amino, di($C_{1-6}$ alkyl)amino, with the proviso that at least one of the phenyl and furyl substituents be selected from (ii) or (iii), and $R_4$ is selected from the group consisting of:

(a) hydrogen;

(b) substituted $C_{1-11}$ alkyl or $C_{2-11}$ alkenyl wherein the substituents are independently selected from the group consisting of hydrogen, hydroxy, halo, $C_{1-6}$ alkyloxy, $C_{1-6}$ alkylthio, $C_{1-6}$ alkylamino, phenyl-$C_{1-6}$ alkylamino, $C_{1-6}$ alkoxycarbonyl; or the pharmaceutically acceptable salts thereof.

29. A compound of the formula 1

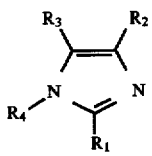

Formula 1 wherein:

$R_1$ is selected from the group consisting of: mono-,di-,and tri-substituted aryl-$C_{0-11}$ alkyl wherein aryl is selected from the group consisting of phenyl, furyl, thienyl, the substituents are selected from the group consisting of:

phenyl, trans-2-phenylethenyl, 2-phenylethynyl, 2-phenylethyl, or in which the said phenyl group is mono- or disubstituted with a member selected from the group consisting of hydroxy, halo, $C_{1-4}$ alkyl and $C_{2-4}$ alkyloxy, $R_2$ and $R_3$ are each independently selected from the group consisting of furyl, mono-, di, and tri-substituted phenyl and furyl wherein the substituents are independently selected from:

(i) halo, trifluoromethyl, $C_{1-6}$ alkyl, (ii) $C_{1-6}$ alkyloxy, (iii) $C_{1-6}$ alkyl-amino, di($C_{1-6}$ alkyl)amino, with the proviso that at least one of the phenyl and furyl substituents be selected from (ii) or (iii).

and $R_4$ is selected from the group consisting of:

(a) hydrogen;

(b) substituted $C_{1-11}$ alkyl or $C_{2-11}$ alkenyl wherein the substituents are independently selected from the group consisting of hydrogen, hydroxy, halo, $C_{1-6}$ alkyloxy, $C_{1-6}$alkylthio, $C_{1-6}$alkylamino, phenyl-$C_{1-6}$ alkylamino, $C_{1-6}$ alkoxycarbonyl; or (c) aryl $C_{0-11}$ alkyl wherein the aryl group is selected from phenyl, imidazolyl, furyl, or thienyl; or the pharmaceutically acceptable salts thereof.

30. A compound of the formula 1

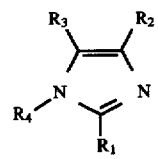

Formula 1 wherein:

$R_1$ is selected from the group consisting of: mono-,di-,and tri-substituted aryl-$C_{0-11}$ alkyl wherein aryl is selected from the group consisting of phenyl, furyl, thienyl, the substituents are selected from the group consisting of: substituted $C_{1-6}$ alkyl, substituted $C_{2-6}$ alkyloxy, substituted $C_{2-6}$ alkylthio, substituted $C_{2-6}$ alkoxycarbonyl, wherein the substituents are selected from the group consisting of $C_{1-6}$ alkoxy, $C_{1-6}$ alkylthio, $R_2$ and $R_3$ are each independently selected from the group consisting of furyl, mono-, di, and tri-substituted phenyl and furyl wherein the substituents are independently selected from:

(i) halo, trifluoromethyl, $C_{1-6}$ alkyl, (ii) $C_{1-6}$ alkyloxy, (iii) $C_{1-6}$ alkyl-amino, di($C_{1-6}$ alkyl)amino, with the proviso that at least one of the phenyl and furyl substituents be selected from (ii) or (iii).

and $R_4$ is selected from the group consisting of:

(a) hydrogen;

(b) substituted $C_{1-11}$ alkyl or $C_{2-11}$ alkenyl wherein the substituents are independently selected from the group consisting of hydrogen, hydroxy, halo, $C_{1-6}$ alkyloxy, $C_{1-6}$ alkylthio, $C_{1-6}$ alkylamino, phenyl-$C_{1-6}$ alkylamino, $C_{1-6}$ alkoxycarbonyl; or (c) aryl $C_{0-11}$ alkyl wherein the aryl group is selected from phenyl, imidazolyl, furyl, or thienyl; or the pharmaceutically acceptable salts thereof.

31. A compound of the formula 1

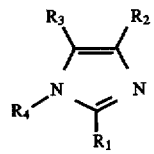

Formula 1 wherein:

$R_1$ is selected from the group consisting of: mono-,di-,and tri-substituted aryl-$C_{0-11}$ alkyl wherein aryl is selected from the group consisting of phenyl, furyl, thienyl, the substituents are selected from the group consisting of;

$C_{1-11}CO_2R_5$, $C_{1-11}CONHR_5$, trans-CH=CHCO$_2R_5$, or trans-CH=CHCONHR$_5$ wherein $R_5$ is $C_{1-11}$alkyl, or phenyl $C_{1-11}$ alkyl, $C_{1-6}$ alkoxycarbonylmethyleneoxy.

$R_2$ and $R_3$ are each independently selected from the group consisting of furyl, mono-, di, and tri-substituted phenyl and furyl wherein the substituents are independently selected from:

(i) halo, trifluoromethyl, $C_{1-6}$ alkyl (ii) $C_{1-6}$ alkyloxy, (iii) $C_{1-6}$ alkyl-amino, di($C_{1-6}$ alkyl)amino, with the proviso that at least one of the phenyl and furyl substituents be selected from (ii) or (iii), and $R_4$ is selected from the group consisting of:

(a) hydrogen;

(b) substituted $C_{1-11}$ alkyl or $C_{2-11}$ alkenyl wherein the substituents are independently selected from the group consisting of hydrogen, hydroxy, halo, $C_{1-6}$ alkyloxy, $C_{1-6}$alkylthio, $C_{1-6}$alkylamino, phenyl-$C_{1-6}$alkylamino, $C_{1-6}$ alkoxycarbonyl; or (c) aryl $C_{0-11}$ alkyl wherein the aryl group is selected from phenyl, imidazolyl, furyl, or thienyl: or the pharmaceutically acceptable salts thereof.

32. A compound of the formula 1

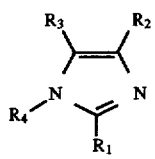

Formula 1 wherein:

$R_1$ is selected from the group consisting of: mono-, di-, and tri-substituted aryl-$C_{0-11}$ alkyl wherein aryl is selected from the group consisting of phenyl, furyl, thienyl, the substituents are selected from the group consisting of:

phenyl, trans-2-phenylethenyl, 2-phenylethynyl, 2-phenylethyl, or in which the said phenyl group is mono- or disubstituted with a member selected from the group consisting of hydroxy, halo, $C_{1-4}$ alkyl and $C_{2-4}$ alkyloxy, $R_2$ and $R_3$ are each independently selected from the group consisting of furyl, mono-, di, and tri-substituted phenyl and furyl wherein the substituents are independently selected from:

(i) halo, trifluoromethyl, $C_{1-6}$ alkyl, (ii) $C_{1-6}$ alkyloxy, (iii) $C_{1-6}$ alkyl-amino, di($C_{1-6}$ alkyl)amino.

with the proviso that at least one of the phenyl and furyl substituents be selected from (ii) or (iii).

and $R_4$ is selected from the group consisting of:

(a) hydrogen;

(b) aryl $C_{0-11}$ alkyl wherein the aryl group is selected from phenyl, imidazolyl, furyl, or thienyl; or the pharmaceutically acceptable salts thereof.

33. A compound of the formula 1

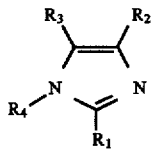

Formula 1 wherein:

$R_1$ is selected from the group consisting of: mono-, di-, and tri-substituted aryl-$C_{0-11}$ alkyl wherein aryl is selected from the group consisting of phenyl, furyl, thienyl, the substituents are selected from the group consisting of:

phenyl, trans-2-phenylethenyl, 2-phenylethynyl, 2-phenylethyl, or in which the said phenyl group is mono- or disubstituted with a member selected from the group consisting of hydroxy, halo, $C_{1-4}$ alkyl and $C_{2-4}$ alkyloxy, $R_2$ and $R_3$ are each independently selected from the group consisting of furyl, mono-, di, and tri-substituted phenyl and furyl wherein the substituents are independently selected from:

(i) halo, trifluoromethyl, $C_{1-6}$ alkyl, (ii) $C_{1-6}$ alkyloxy, (iii) $C_{1-6}$ alkyl-amino, di($C_{1-6}$ alkyl)amino;

with the proviso that at least one of the phenyl and furyl substituents be selected from (ii) or (iii).

and $R_4$ is selected from the group consisting of:

(a) hydrogen;

(b) substituted $C_{1-11}$ alkyl or $C_{2-11}$ alkenyl wherein the substituents are independently selected from the group consisting of hydrogen, hydroxy, halo, $C_{1-6}$ alkyloxy, $C_{1-6}$ alkylthio, $C_{1-6}$ alkylamino, phenyl-$C_{1-6}$ alkylamino, $C_{1-6}$ alkoxycarbonyl; or the pharmaceutically acceptable salts thereof.

34. A compound of the formula 1

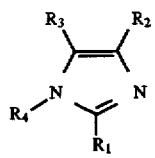

Formula 1 wherein:

$R_1$ is selected from the group consisting of: substituted $C_{1-11}$ alkyl or substituted $C_{2-11}$ alkenyl, wherein the substituents are selected from the group consisting of hydroxy, $C_{1-6}$ alkyloxy; or $R_2$ and $R_3$ are each independently selected from the group consisting of furyl, mono-, di, and hi-substituted phenyl and furyl wherein the substituents are independently selected from:

(i) halo, trifluoromethyl, $C_{1-6}$ alkyl, (ii) $C_{1-6}$ alkyloxy, (iii) $C_{1-6}$ alkyl-amino, di($C_{1-6}$ alkyl)amino.

with the proviso that at least one of the phenyl and furyl substituents be selected from (ii) or (iii).

and $R_4$ is selected from the group consisting of:

(a) hydrogen;

(b) aryl $C_{0-11}$ alkyl wherein the aryl group is selected from phenyl, imidazolyl, furyl, or thienyl; or the pharmaceutically acceptable salts thereof.

35. A compound of the formula 1

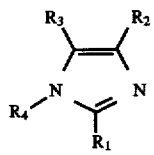

Formula 1 wherein:

$R_1$ is selected from the group consisting of: substituted $C_{1-11}$ alkyl or substituted $C_{2-11}$ alkenyl, wherein the substituents are selected from the group consisting of hydroxy, $C_{1-6}$ alkyloxy; or $R_2$ and $R_3$ are each independently selected from the group consisting of furyl, mono-, di, and tri-substituted phenyl and furyl wherein the substituents are independently selected from:

(i) halo, trifluoromethyl, $C_{1-6}$ alkyl, (ii) alkyloxy, (iii) $C_{1-6}$ alkyl-amino, di($C_{1-6}$ alkyl)amino, with the proviso that at least one of the phenyl and furyl substituents be selected from (ii) or (iii).

and $R_4$ is selected from the group consisting of:

(a) hydrogen;

(b) substituted $C_{1-11}$ alkyl or $C_{2-11}$ alkenyl wherein the substituents are independently selected from the group consisting of hydrogen, hydroxy, halo, $C_{1-6}$ alkyloxy, $C_{1-6}$ alkylthio, $C_{1-6}$ alkylamino, phenyl-$C_{1-6}$ alkylamino, $C_{1-6}$ alkoxycarbonyl; or the pharmaceutically acceptable salts thereof.

36. A compound of the formula 1

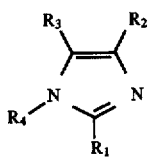

Formula 1 wherein:

$R_1$ is selected from the group consisting of:

(a) substituted $C_{1-6}$ alkyl or substituted $C_{2-6}$ alkenyl, wherein the substituents are selected from the group consisting $C_{1-6}$ alkyloxy; or (b) mono-, di-, and tri-substituted aryl-$C_{0-11}$ alkyl wherein aryl is selected from the group consisting of phenyl, the substituents are selected from the group consisting of:

$C_{1-4}$ alkyl and $C_{2-4}$ alkyloxy, $C_{1-11}CO_2R_5$, $C_{1-11}CONHR_5$, trans-$CH=CHCO_2R_5$, or trans-$CH=CHCONHR_5$ wherein $R_5$ is $C_{1-11}$ alkyl, or phenyl $C_{1-11}$ alkyl, $R_2$ and $R_3$ are each independently selected from the group consisting of, mono-, di, and tri-substituted phenyl wherein the substituents are independently selected from:

(ii) $C_{1-6}$ alkyloxy, (iii) $C_{1-6}$ alkyl-amino, di($C_{1-6}$ alkyl)amino, and $R_4$ is selected from the group consisting of:

(a) hydrogen;

(b) substituted $C_{1-6}$alkyl or $C_{2-6}$alkenyl wherein the substituents are independently selected from the group consisting of hydrogen, $C_{1-6}$ alkyloxy, $C_{1-6}$alkylamino, or aryl $C_{0-11}$ alkyl wherein the aryl group is selected from phenyl, or the pharmaceutically acceptable salts thereof.

37. A compound of the formula 1

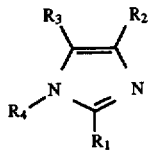

Formula 1 wherein:

$R_1$ is selected from the group consisting of:

(a) substituted $C_{2-6}$ alkenyl, $C_{1-6}$ alkyl wherein the substituents are selected from the group consisting $C_{1-6}$ alkyloxy; or (b) mono- substituted aryl-$C_{0-11}$ alkyl wherein aryl is selected from the group consisting of phenyl, the substituents are selected from the group consisting of;

$C_{1-4}$ alkyl and $C_{2-4}$ alkyloxy, $C_{1-6}CO_2R_5$, trans-$CH=CHCO_2R_5$, wherein $R_5$ is $C_{1-6}$alkyl, or phenyl $C_{1-6}$ alkyl, $R_2$ and $R_3$ are each independently selected from the group consisting of, mono-, di, and tri-substituted phenyl wherein the substituents are independently selected from:

(ii) $C_{1-6}$ alkyloxy, (iii) $C_{1-6}$ alkyl-amino, di($C_{1-6}$ alkyl)amino, and $R_4$ is selected from the group consisting of:

(a) hydrogen;

(b) $C_{1-6}$ alkyloxy, $C_{1-6}$ alkylamino, or (c) aryl $C_{0-6}$ alkyl wherein the aryl group is selected from phenyl, imidazol or the pharmaceutically acceptable salts thereof.

38. A compound of the formula 1

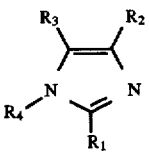

Formula 1 wherein:

$R_1$ is selected from the group consisting of:

(a) substituted $C_{2-6}$ alkenyl, $C_{2-6}$ alkyl wherein the substituents are selected from the group consisting $C_{1-6}$ alkyloxy; or (b) mono- substituted aryl-$C_{0-6}$ alkyl wherein aryl is selected from the group consisting of phenyl, the substituents are selected from the group consisting of:

$C_{1-4}$ alkyl and $C_{2-4}$ alkyloxy, $C_{1-6}CO_2R_5$, trans-$CH=CHCO_2R_5$, wherein $R_5$ is $C_{1-5}$alkyl, or phenyl $C_{1-6}$ alkyl, $R_2$ and $R_3$ are each independently selected from the group consisting of, mono-, di, and tri-substituted phenyl wherein the substituents are independently selected from:

$C_{1-6}$ alkyl-amino, di($C_{1-6}$ alkyl)amino, and $R_4$ is selected from the group consisting of: hydrogen; or the pharmaceutically acceptable salts thereof.

39. A compound of the formula 1

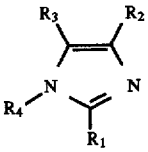

Formula 1 wherein:

$R_1$ is selected from the group consisting of:

(a) substituted $C_{2-6}$ alkenyl $C_{2-6}$ alkyl wherein the substituents are selected from the group consisting $C_{1-6}$ alkyloxy; or (b) mono- substituted aryl-$C_{0-11}$ alkyl wherein aryl is selected from the group consisting of phenyl, the substituents are selected from the group consisting of:

$C_{1-4}$ alkyl and $C_{2-4}$ alkyloxy, $C_{1-6}CO_2R_5$, trans-$CH=CHCO_2R_5$, wherein $R_5$ is $C_{1-6}$alkyl, or phenyl $C_{1-6}$ alkyl, $R_2$ and $R_3$ are each independently selected from the group consisting of, mono substituted phenyl wherein the substituents are independently selected from:

$C_{1-6}$ alkyl-amino, di($C_{1-6}$ alkyl)amino, $C_{1-6}$ alkyloxy and $R_4$ is selected from the group consisting of: hydrogen, $C_{1-6}$ alkyloxy, $C_{1-6}$alkylamino, or aryl $C_{0-6}$ alkyl wherein the aryl group is selected from phenyl, imidazol or the pharmaceutically acceptable salts thereof.

* * * * *